US009233138B2

(12) United States Patent
Abrams et al.

(10) Patent No.: US 9,233,138 B2
(45) Date of Patent: Jan. 12, 2016

(54) COMPOSITIONS FOR PROMOTING HIV-1 VIROLYSIS AND METHODS USING SAME

(71) Applicant: Drexel University, Philadelphia, PA (US)

(72) Inventors: Cameron Frank Abrams, Philadelphia, PA (US); Irwin M. Chaiken, Gladwyne, PA (US); Mark R. Contarino, Philadelphia, PA (US); Bibek Parajuli, Philadelphia, PA (US); Adel Ahmed Rashad Ahmed, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/520,995

(22) Filed: Oct. 22, 2014

(65) Prior Publication Data

US 2015/0111814 A1  Apr. 23, 2015

Related U.S. Application Data

(60) Provisional application No. 61/893,966, filed on Oct. 22, 2013.

(51) Int. Cl.
*A61K 38/16* (2006.01)
*C12N 7/00* (2006.01)
*C07K 14/195* (2006.01)
*C07K 14/005* (2006.01)
*A61K 45/06* (2006.01)
*A61K 47/48* (2006.01)

(52) U.S. Cl.
CPC ............. *A61K 38/164* (2013.01); *A61K 38/162* (2013.01); *A61K 45/06* (2013.01); *A61K 47/48246* (2013.01); *A61K 47/48338* (2013.01); *C07K 14/005* (2013.01); *C07K 14/195* (2013.01); *C12N 7/00* (2013.01); *C07K 2319/70* (2013.01); *C12N 2740/16033* (2013.01)

(58) Field of Classification Search
None
See application file for complete search history.

(56) References Cited

U.S. PATENT DOCUMENTS

| | | | |
|---|---|---|---|
| 7,556,808 B2 | 7/2009 | Hosahudya et al. | |
| 7,655,464 B2 | 2/2010 | Hosahudya et al. | |
| 8,092,805 B2 | 1/2012 | Gopi et al. | |
| 8,575,095 B2 * | 11/2013 | Chaiken ................... | C07K 7/06 514/1.1 |
| 2006/0135746 A1 | 6/2006 | Hosahudya et al. | |
| 2006/0165751 A1 | 7/2006 | Chudzik et al. | |
| 2007/0054337 A1 | 3/2007 | Ferning et al. | |
| 2010/0216721 A1 | 8/2010 | Gopi et al. | |
| 2012/0165250 A1 | 6/2012 | Chaiken et al. | |
| 2013/0274178 A1 | 10/2013 | Chalken et al. | |
| 2014/0050793 A1 | 2/2014 | Chaiken et al. | |

FOREIGN PATENT DOCUMENTS

WO  2008150444 A1  12/2008

OTHER PUBLICATIONS

Contarino, et al., "Chimeric Cyanovirin-MPER Recombinantly Engineered Proteins Cause Cell-Free Virolysis of HIV-1", Antimicrobial Agents and Chemotherapy, Oct. 2013, 57(10): 4743-4750.
Bryson, et al., "Crystallographic Definition of the Epitope Promiscuity of the Broadly Neutralizing Anti-Human Immunodeficiency Virus Type 1 Antibody 2F5: Vaccine Design Implications", Journal of Virology, Nov. 2009, 83 (22): 11862-11875.
Boyd, et al., "Discovery of Cyanovirin-N, a Novel Human Immunodeficiency Virus-Inactivating Protein That Binds Viral Surface Envelope Glycoprotein gp120: Potential Applications to Microbicide Development," Antimicrobial Agents and Chemotherapy, Jul. 1997, 41(7): 1521-1530.
Cocklin, et al., "Broad-Spectrum Anti-Human Immunodeficiency Virus (HIV) Potential of a Peptide HIV Type 1 Entry Inhibitor," Journal of Virology, Apr. 2007, 81 (7): 3645-3648.
Ferrer et al., "Peptide Ligands to Human Immunodeficiency Virus Type 1 gp120 Identified from Phage Display Libraries," Journal of Virology, Jul. 1999, 73(7): 5795-5802.
Gopi, et al., "Click Chemistry on Azidoproline: High Affinity Dual Antagonist for HIV-1 Envelope Glycoprotein gp120," ChemMedChem, 2006, 1: 54-57.
Gopi, et al., "Introducing metallocene into a triazole peptide conjugate reduces its off-rate and ehnahnces its affinity and ativiral potency for HIV-1 gp120", J. Mol. Recgonit, 2009 (published online May 22, 2008) 22: 169-174.
Guo, et al. "Biochemical and Genetic Characterizations of a Novel Human Immunodeficiency Virus Type 1 Inhibitor That Blocks gp120-CD4 Interactions", Journal of Virology, Oct. 2003, 77(19): 10528-10536.
Lin, et al., "A small molecule HIV-1 inhibitor that targets the HIV-1 envelope and inhibits CD4 receptor binding", PNAS, Sep. 16, 2003, 100 (19): 11013-11018.
McKnight, et al., "Blocking the docking of HIV-1", PNAS, Sep. 16, 2003, 100(19): 10581-10582.
Shahzad-Ul-Hussan, et al., "Solution Structure of the Monovalent Lectin Microvirin in Complex with Manα(1-2) Man Provides a Basis for Anti-HIV Activity with Low Toxicity", The Journal of Biological Chemistry, Jun. 10, 2011, 286 (23): 20788-20796.
Si, et al. "Small-molecule inhibitors of HIV-1 entry block receptor-induced conformational changes in the viral envelope glycoprotiens", PNAS, Apr. 6, 2004, 1001 (14): 5036-5041.
Tsai, et al., "Cynovirin-N Gel as a Topical Microbicide Prevents Rectal Transmission of SHIV89.6P in Macaques", Aids Research and Human Retroviruses, 2003, 19(7): 535-541.
Tsai, et al., "Cynovirin-N Inhibits AIDS Virus Infections in Vaginal Transmission Models", Aids Research and Human Retroviruses, 2004, 20(1): 11-18.
Veazy, et al., "Protection of macaques from vaginal SHIV challenge by vaginally delivered inhibitors of virus-cell fusion", Nature, Nov. 3, 2005, 438: 99-102.

* cited by examiner

*Primary Examiner* — Thomas S Heard
(74) *Attorney, Agent, or Firm* — Saul Ewing LLP; Kathryn Doyle; Domingos J. Silva

(57) ABSTRACT

The present invention includes compounds that are useful for treating or preventing a HIV-1 infection in a mammal. In certain embodiments, the compounds cause cell-free virolysis of an HIV-1 virus. The presented invention further includes a method of causing virolysis of a virus using the compounds described therein. The presented invention further includes a method of treating or preventing an HIV-1 infection in a mammal in need thereof using the compositions described therein.

27 Claims, 19 Drawing Sheets

Fig. 1C

```
aattttgtttaactttaagaaggagatatacatatgaaatacctgctgccgaccgctgct
 N   F   V   -   L   -   E   G   D   I   H   M   K   Y   L   L   P   T   A   A
gctggtctgctgctcctcgctacccagccggcgatggcccttggtaaattctcccagacc
 A   G   L   L   L   A   T   Q   P   A   M   A   L   G   K   F   S   Q   T
tgctacaactccgctatccagggttccgttctgacctccacctgcgaacgtaccaacggt
 C   Y   N   S   A   I   Q   G   S   V   L   T   S   T   C   E   R   T   N   G
ggttacaacacctcctccatcgacctgaactccgttatcgaaaacgttgacggttccctg
 G   Y   N   T   S   S   I   D   L   N   S   V   I   E   N   V   D   G   S   L
aaatggcagccgtccaacttcatcgaaacctgccgtaacacccagctggctggttcctcc
 K   W   Q   P   S   N   F   I   E   T   C   R   N   T   Q   L   A   G   S   S
gaactggctgctgaatgcaaaaccgtgctcagcagttcgtttccaccaaaatcaacctg
 E   L   A   A   E   C   K   T   R   A   Q   Q   F   V   S   T   K   I   N   L
gacgaccacatcgctaacatcgacggtaccctgaaatacgaagggtctggtggcggaggg
 D   D   H   I   A   N   I   D   G   T   L   K   Y   E   G   S   G   G   G
tcgggcggaggtggaagcggaggtggcggtagtggtggaggcggatcccatcatcatcat
 S   G   G   G   S   G   G   G   S   G   G   G   S   H   H   H   H
catcatgacaaatgggcaagtttgtggaattggtttgaaataacagaatggctgtggtat
 H   H   D   K   W   A   S   L   W   N   W   F   E   I   T   E   W   L   W   Y
ataaaataataataaaagcttgcggccgcactcgagcaccaccaccaccactgagat
 I   K   -   -   -   K   L   A   A   L   E   H   H   H   H   H   -   D
```

Fig. 1D

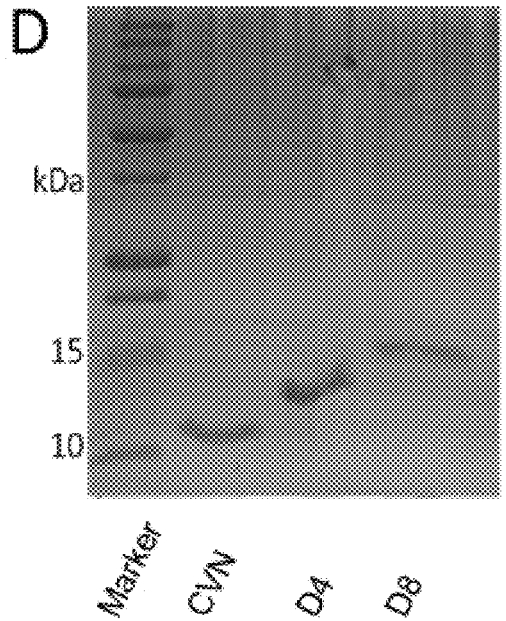

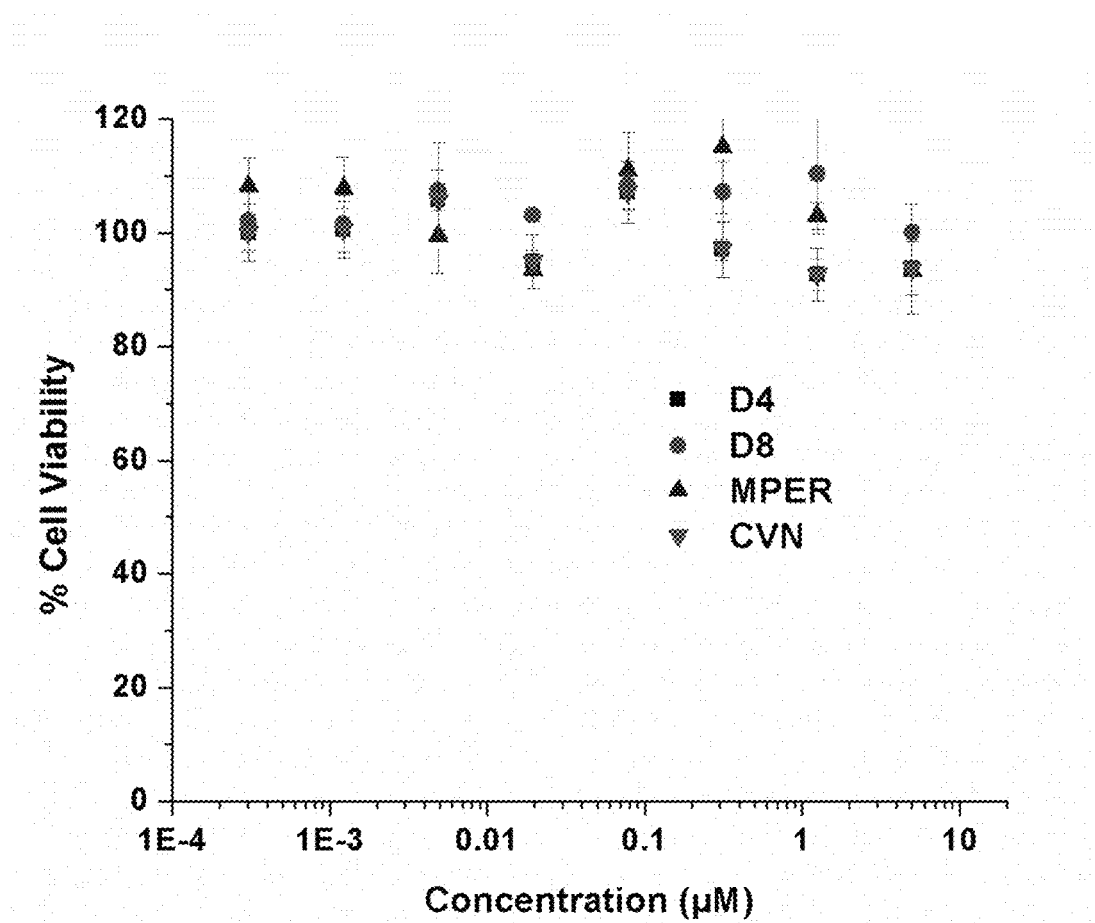

Fig. 7A
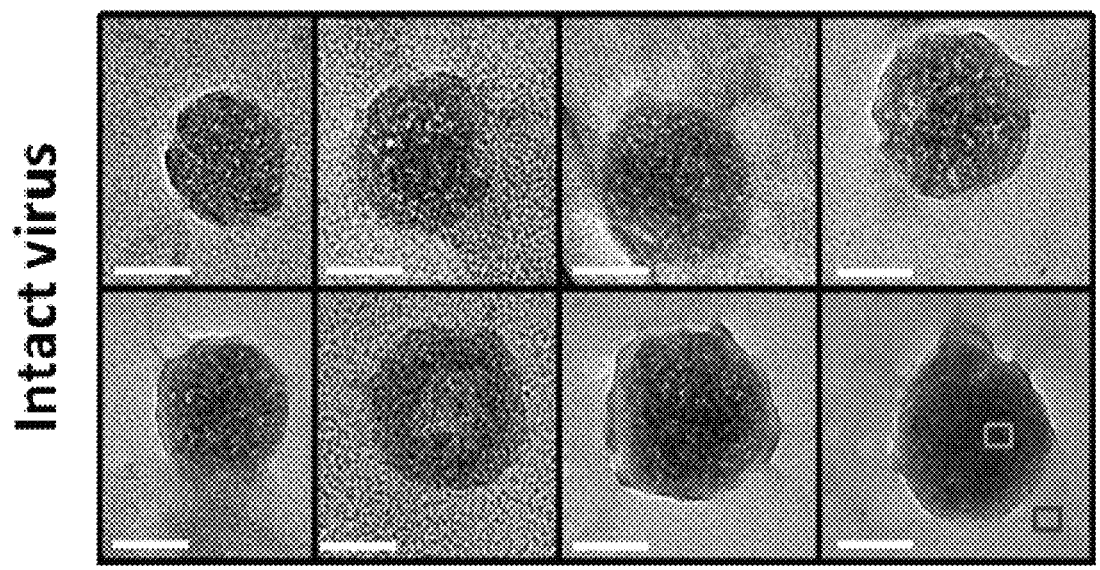
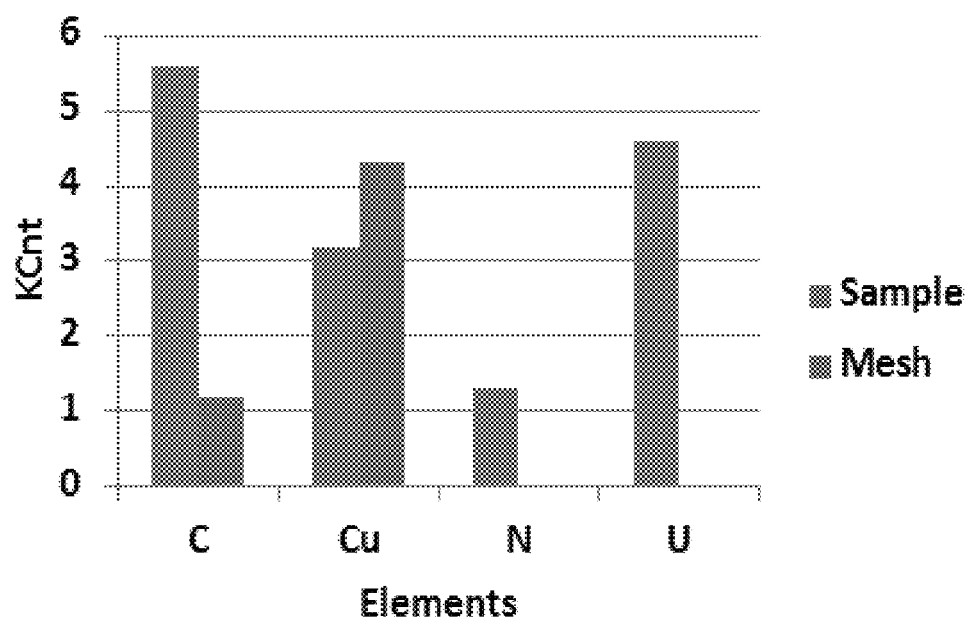

Fig. 7B
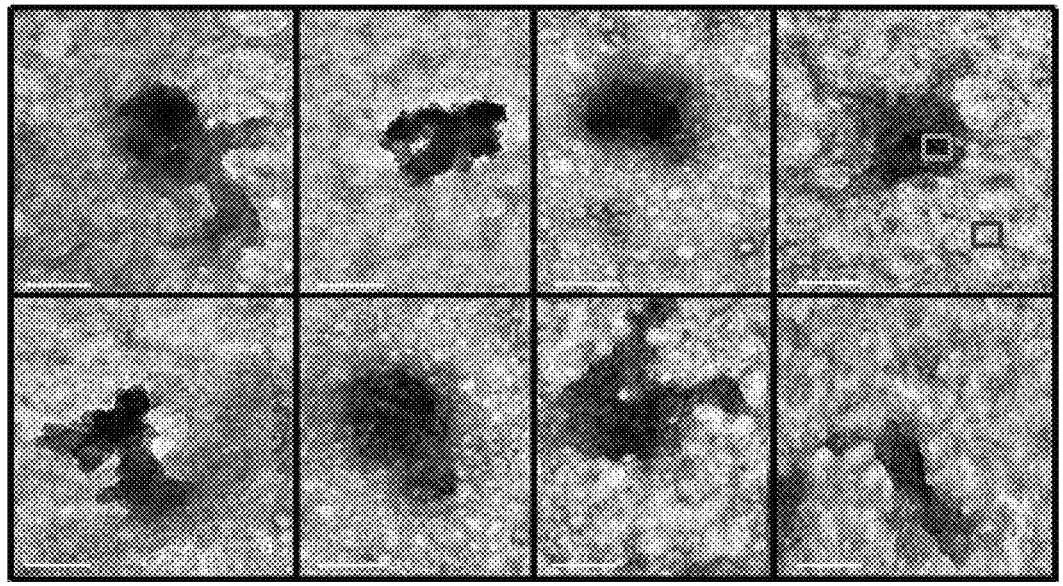
D4
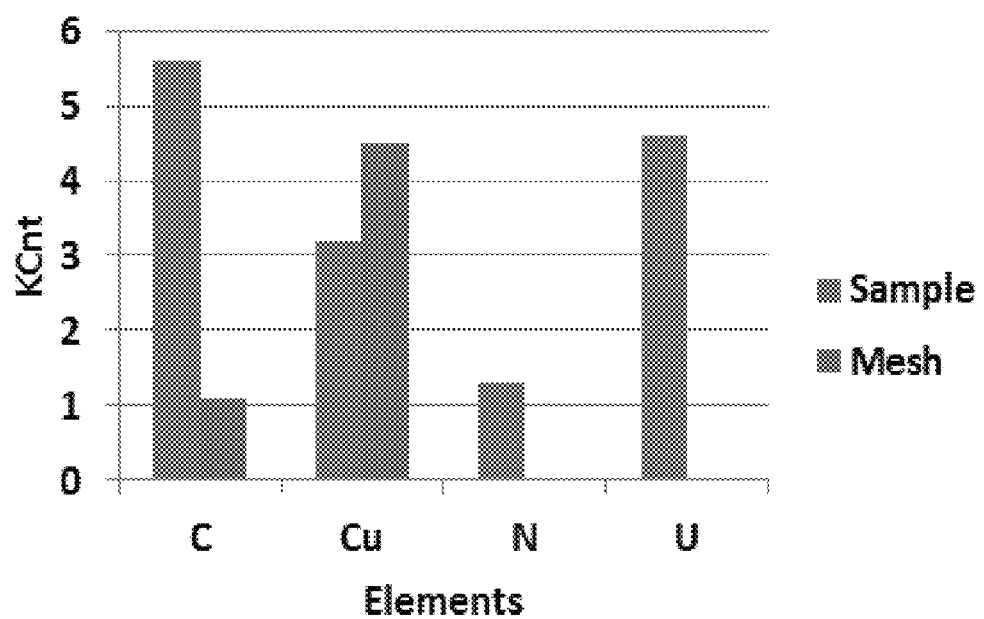

Fig. 7C
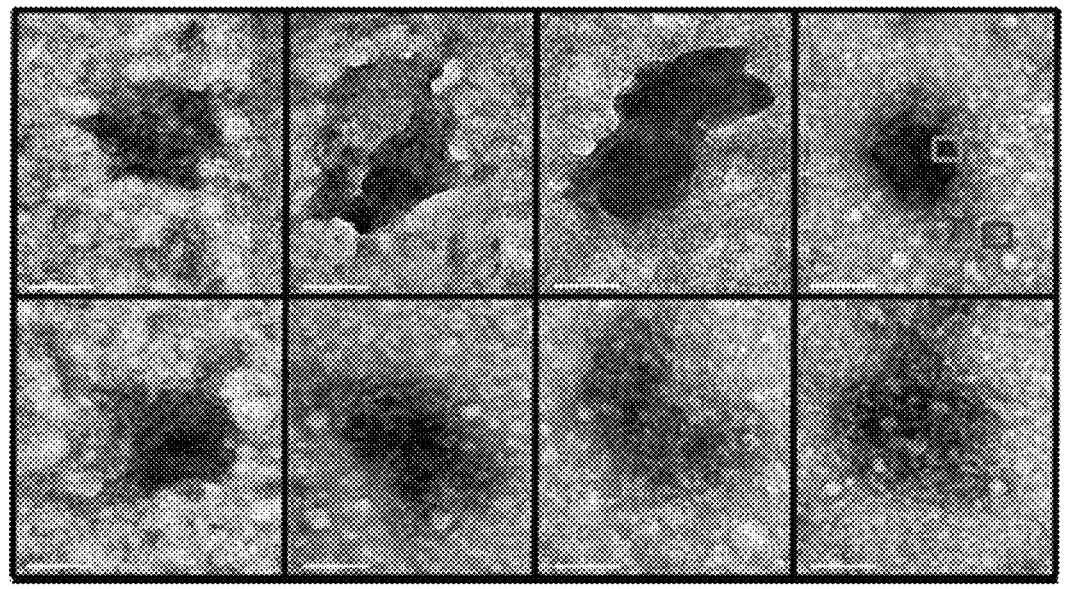
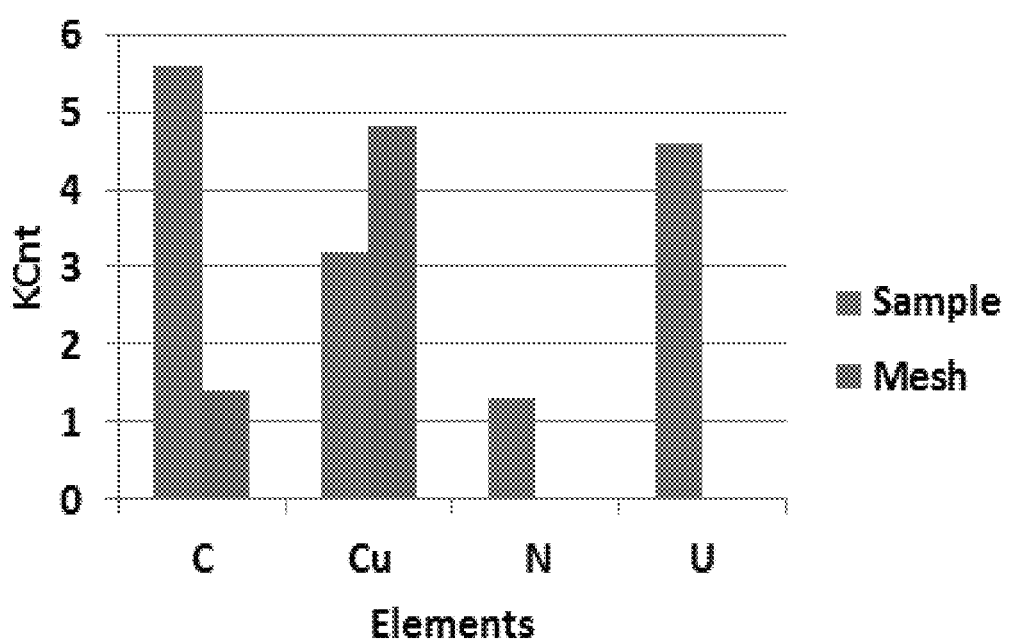

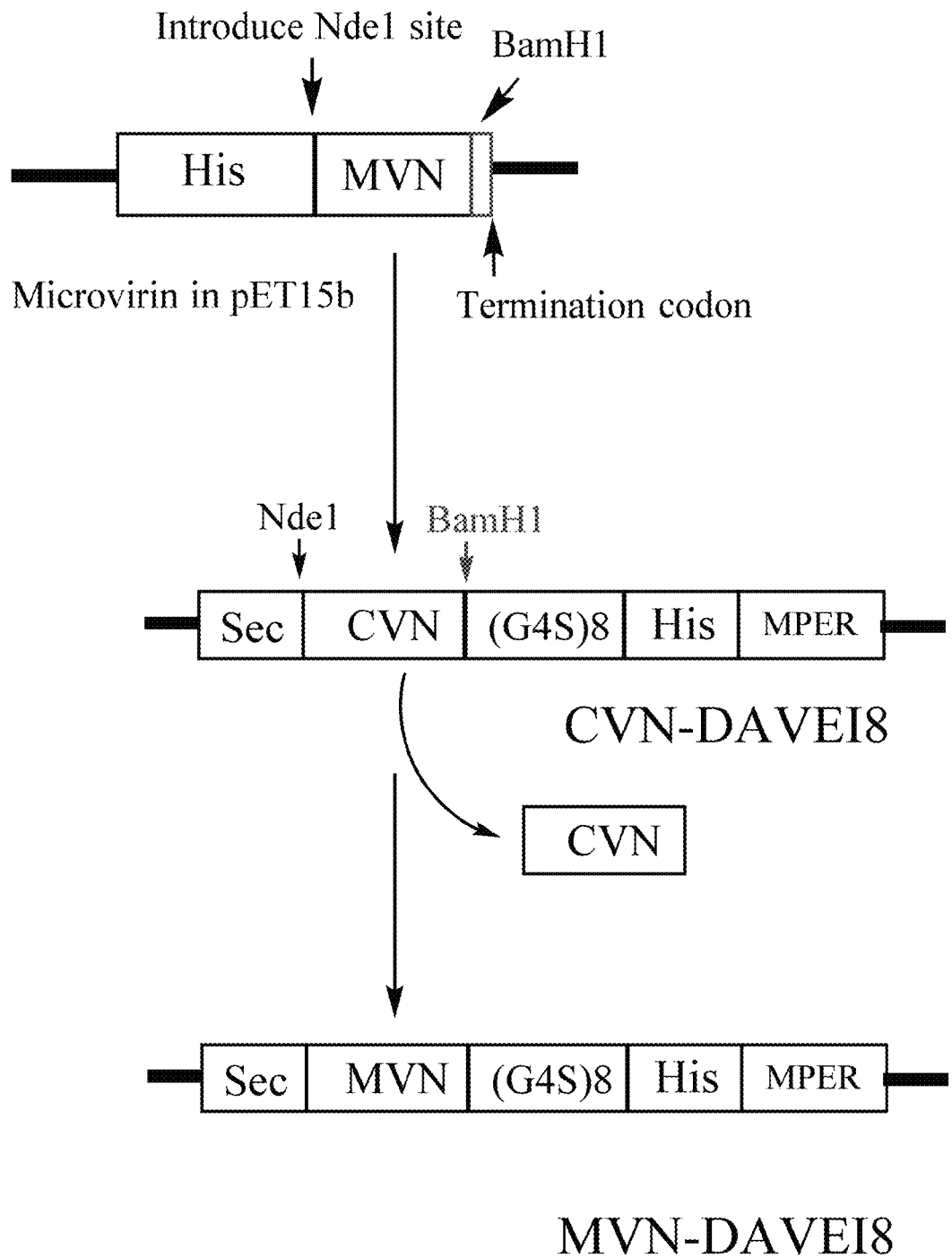

| Case | WT gp160-MVN resistant gp160 (μg) | % of spikes | | | |
|---|---|---|---|---|---|
| 1 | 4:0 | 100 | 0 | 0 | 0 |
| 2 | 3:1 | 42 | 42 | 14 | 2 |
| 3 | 2:2 | 12.5 | 37.5 | 37.5 | 12.5 |
| 4 | 1:3 | 2 | 14 | 42 | 42 |
| 5 | 0:4 | 0 | 0 | 0 | 100 |

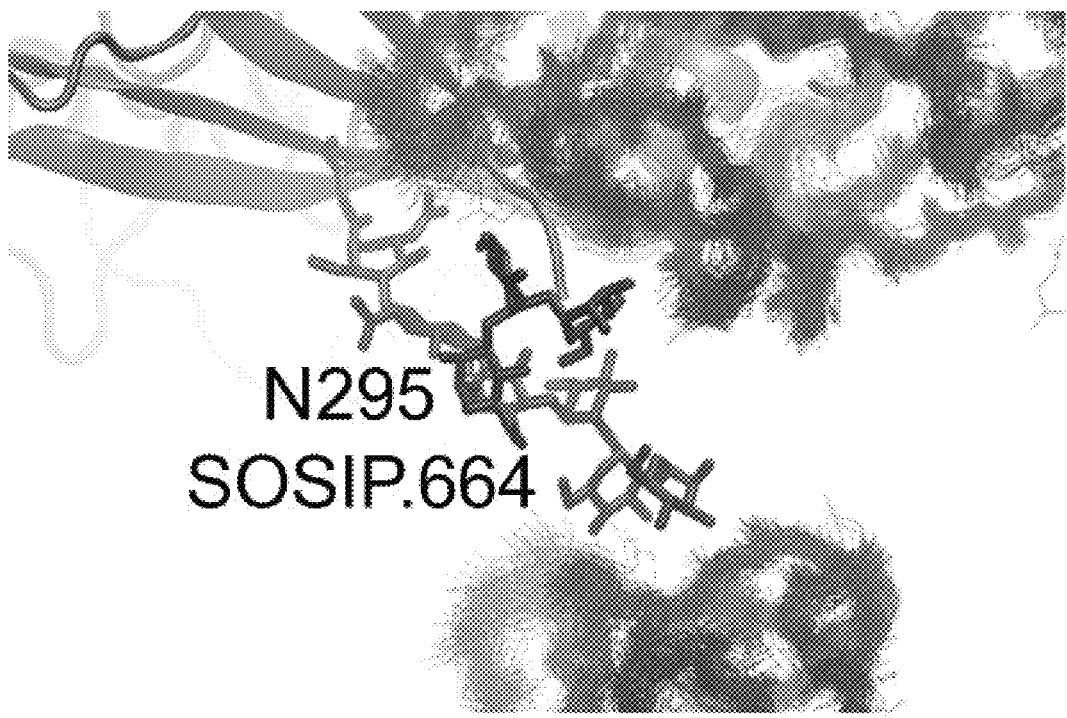
Fig. 12
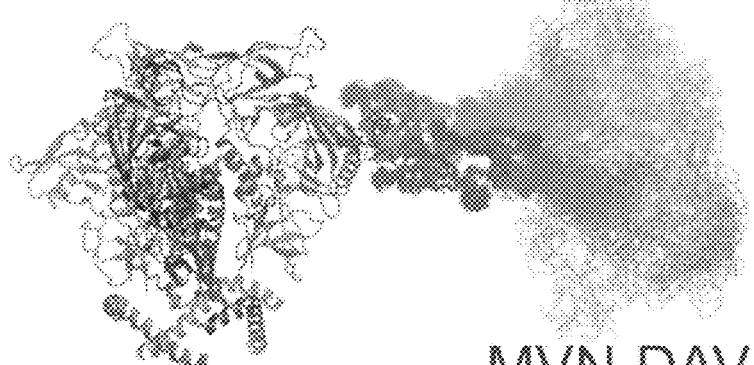

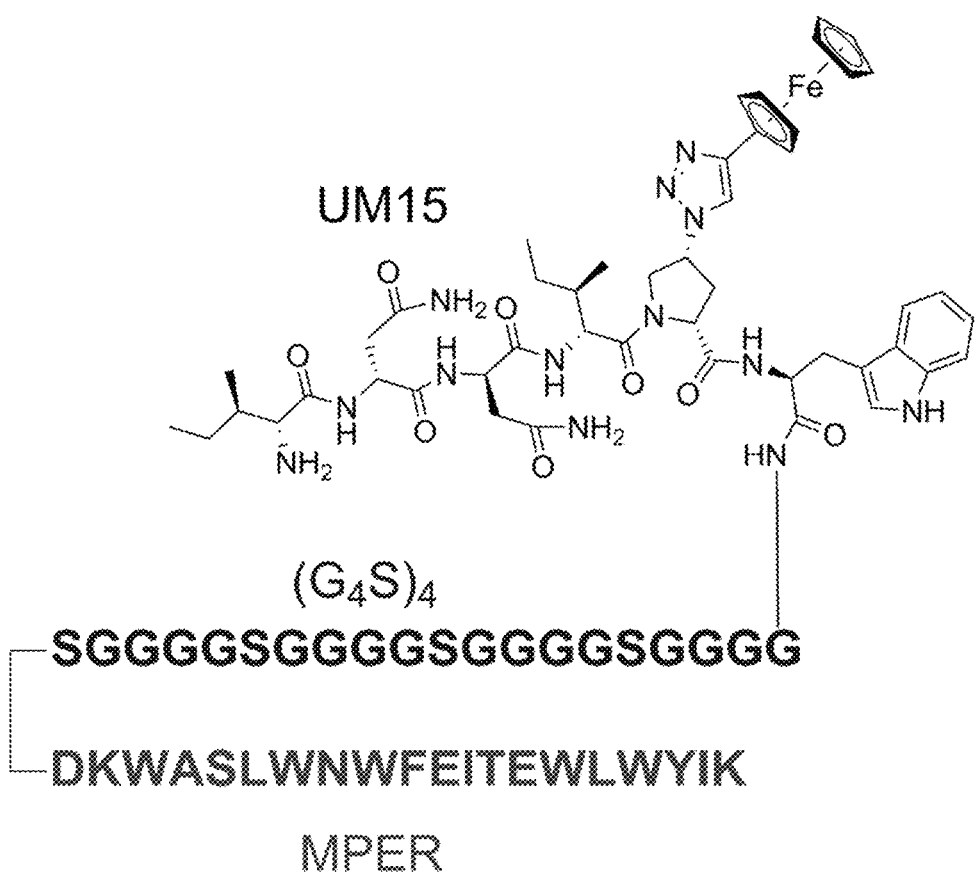

COMPOSITIONS FOR PROMOTING HIV-1 VIROLYSIS AND METHODS USING SAME

CROSS-REFERENCE TO RELATED APPLICATIONS

The present application claims priority under 35 U.S.C. §119(e) to U.S. Provisional Patent Application No. 61/893,966, filed Oct. 22, 2013, which application is incorporated herein by reference in its entirety.

STATEMENT REGARDING FEDERALLY SPONSORED RESEARCH OR DEVELOPMENT

This invention was made with government support under CBET-0853680 awarded by National Science Foundation, and P01 GM056550 and R01 AI084117 awarded by National Institutes of Health. The government has certain rights in the invention.

BACKGROUND OF THE INVENTION

The human immunodeficiency virus-1 (HIV-1) is responsible for a global epidemic, with over 33 million infected people worldwide. The lifecycle of HIV-1 has been extensively studied in the hope of identifying a therapeutic intervention that blocks viral transmission or viability. As an example, the Highly Active Anti-Retroviral Therapy (HAART) is a therapeutic approach targeting one or more stages of the HIV-1 life cycle. Favorable clinical results with HAART have shown that targeting different stages of the viral life cycle simultaneously may reduce the viral evolutionary escape mechanism that leads to drug resistance. HAART has proven effective at delaying the onset of AIDS in HIV-positive individuals, but does not provide a cure for the infection itself.

Despite decades of research, no vaccine- or microbicide-based approaches for preventing HIV-1 transmission to non-infected individuals are yet available. Even within the current space of prospective microbicides, there are no examples of clinically used agents or combinations of agents that directly and specifically destroy mature HIV-1 particles before they gain entry to a target cell. In fact, the leading microbicidal candidate is based on tenofovir, a reverse-transcriptase inhibitor. Thus, at this time there is no known therapeutically effective agent that specifically prevents HIV-1 entry and irreversibly destroys the virus, e.g., a therapeutic agent that directly and specifically destroys mature HIV-1 particles before they gain entry to a target cell.

A mature HIV-1 virion is an approximately one-attoliter-sized bilayer-enveloped packet of cytoplasm stolen from the cell from which the virion budded, surrounding the RNA-containing nucleocapsid. HIV-1 enters target cells via interactions between the viral envelope protein spike, Env, with the surface-expressed CD4 receptor and a chemokine co-receptor (CCR5 or CXCR4). Env is a metastable heterotrimeric protein complex of three transmembrane gp41 subunits anchored to the viral membrane and three labile gp120 subunits that interface with gp41. The infection process starts with gp120 binding to CD4 and induction of a conformational change that exposes the co-receptor binding site. In turn, the fusion peptide sequence on gp41 inserts into the host membrane. Subsequently, gp41 transitions from a "pre-hairpin" complex into a collapsed, thermodynamically stable six-helix bundle, with the three N-terminal heptad repeats of each gp41 protomer forming the core and the three C-terminal heptad repeats folded into grooves along the outside of this core. This refolding process evidently brings the N- and C-termini of gp41 close together and, in so doing, brings the apposing membranes into close enough proximity that fusion is initiated. Spike-mediated fusion of viral and cellular membranes requires that one of its functions is to induce poration of viral membrane.

There is a need in the art to develop novel potent compositions that promote cell-free virolysis of HIV-1 virus. Such compositions would be useful for the prevention or treatment of HIV-1 infection. The present invention fulfills this need.

BRIEF SUMMARY OF THE INVENTION

The invention includes a compound of formula (I), or a salt or solvate thereof: BINDER-LINKER-SEQ ID NO:3 (I), wherein in (I) the BINDER binds to gp120, and the LINKER covalently connects the C-terminus of the BINDER and the N-terminus of SEQ ID NO:3. The invention further includes a pharmaceutical composition comprising the compound of the invention and at least one pharmaceutically acceptable carrier. The invention further includes a method of promoting HIV-1 virolysis. The invention further includes a method of treating or preventing HIV-1 infection in a mammal in need thereof.

In certain embodiments, the BINDER comprises at least one selected from the group consisting of: SEQ ID NO:1; SEQ ID NO:12; SEQ ID NO:22 ($X_1X_2X_3NIXWX_4$) (III), wherein in (III) $X_1$ is absent or E, $X_2$ is selected from the group consisting of F, K, E, R and Cit, $X_3$ is N or I, $X_4$ is S or T; SEQ ID NO:23 (RINNIXW); SEQ ID NO:24 (INNIXW); SEQ ID NO:25 (NNIXWS); SEQ ID NO:26 (INIXWS); and SEQ ID NO:27 (NNIXW); wherein X is the modified proline of formula (IV)

wherein in (IV) R is selected from the group consisting of naphthyl, p-methyl phenyl, p-ethyl phenyl, 2-phenylethyl and metallocene.

In certain embodiments, the LINKER covalently connects the N-terminus of SEQ ID NO:3 and the C-terminus of a sequence selected from the group consisting of SEQ ID NOs: 1, 12 and 22-27. In other embodiments, the metallocene is ferrocene.

In certain embodiments, the LINKER comprises a peptide of formula (II), or a salt or solvate thereof: LINKER1-(LINKER2)$_n$ (II), wherein the LINKER1 comprises 1 to 60 amino acid residues; LINKER 2 comprises (His)$_6$ (SEQ ID NO:5) or AspTyrLysAspAspAspAspLys (SEQ ID NO:9), and 'n' is 0 or 1.

In certain embodiments, the LINKER1 comprises 10 to 50 neutral amino acid residues selected from the group consisting of glycine and serine residues. In other embodiments, the LINKER1 comprises 2 to 10 repeating units of a pentapeptide consisting of neutral amino acid residues. In yet other embodiments, the neutral amino acid residues are selected from the group consisting of glycine and serine residues. In yet other embodiments, the LINKER1 comprises (SEQ ID NO:6)$_m$ or (SEQ ID NO:10)-(SEQ ID NO:6)$_m$, wherein 'm' is an integer ranging from 2 to 10. In yet other embodiments, the LINKER1 comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$ or Ser-(SEQ ID NO:6)$_2$-Gly-(SEQ ID NO:6)-Gly-(SEQ ID NO:6)$_5$. In yet other embodiments, the LINKER comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$, Ser-(SEQ ID NO:6)$_2$-Gly-(SEQ ID NO:6)-Gly-(SEQ ID NO:6)$_5$, (SEQ ID NO:6)$_4$-(SEQ ID NO:5), (SEQ ID NO:10)-(SEQ ID NO:6)$_4$-(SEQ ID NO:5), (SEQ ID NO:6)$_8$-(SEQ ID NO:5), (SEQ ID NO:10)-(SEQ ID NO:6)$_8$-(SEQ ID NO:5), Ser-(SEQ ID NO:6)$_2$-Gly-(SEQ ID NO:6)-Gly-(SEQ ID NO:6)$_5$-(SEQ ID NO:5), (SEQ ID NO:6)$_4$-(SEQ ID NO:9), (SEQ ID NO:10)-(SEQ ID NO:6)$_4$-(SEQ ID NO:9), (SEQ ID NO:6)$_8$-(SEQ ID NO:9), (SEQ ID NO:10)-(SEQ ID NO:6)$_8$-(SEQ ID NO:9), or Ser-(SEQ ID NO:6)$_2$-Gly-(SEQ ID NO:6)-Gly-(SEQ ID NO:6)$_5$-(SEQ ID NO:9).

In certain embodiments, the compound of formula (I) comprises at least one selected from the group consisting of SEQ ID NO:1-(SEQ ID NO:10)$_{0-1}$-(SEQ ID NO:6)$_4$-SEQ ID NO:5-SEQ ID NO:3; SEQ ID NO:1-(SEQ ID NO:10)$_{0-1}$-(SEQ ID NO:6)$_4$-SEQ ID NO:3; SEQ ID NO:1-(SEQ ID NO:10)$_{0-1}$-(SEQ ID NO:6)$_8$-SEQ ID NO:5-SEQ ID NO:3; SEQ ID NO:1-(SEQ ID NO:10)$_{0-1}$-(SEQ ID NO:6)$_8$-SEQ ID NO:3; SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:3; SEQ ID NO:1-Ser-(SEQ ID NO:6)$_2$-Gly-(SEQ ID NO:6)-Gly-(SEQ ID NO:6)$_5$-SEQ ID NO:3; SEQ ID NO:12-(SEQ ID NO:10)$_{0-1}$-(SEQ ID NO:6)$_4$-SEQ ID NO:5-SEQ ID NO:3; SEQ ID NO:12-(SEQ ID NO:10)$_{0-1}$-(SEQ ID NO:6)$_4$-SEQ ID NO:3; SEQ ID NO:12-(SEQ ID NO:10)$_{0-1}$-(SEQ ID NO:6)$_8$-SEQ ID NO:5-SEQ ID NO:3; SEQ ID NO:12-(SEQ ID NO:10)$_{0-1}$-(SEQ ID NO:6)$_8$-SEQ ID NO:3; SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:3; SEQ ID NO:12-Ser-(SEQ ID NO:6)$_2$-Gly-(SEQ ID NO:6)-Gly-(SEQ ID NO:6)$_5$-SEQ ID NO:3; and any combinations thereof.

In certain embodiments, the compositions of the invention further comprise at least one additional agent useful for treating HIV infections. In other embodiments, the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof.

In certain embodiments, the methods of the invention comprise contacting HIV-1 with an effective amount of at least one compound of the present invention, whereby HIV-1 undergoes virolysis. In other embodiments, the HIV-1 is present in the body of a mammal.

In certain embodiments, the mammal is human.

In certain embodiments, the methods of the invention comprise administering to the mammal a therapeutically effective amount of at least one compound of the present invention, whereby administration of the compound treats or prevents HIV-1 infection.

In certain embodiments, the mammal is further administered at least one additional agent useful for treating HIV infections. In other embodiments, the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof.

In certain embodiments, the at least one additional agent and the compound are co-formulated. In other embodiments, the compound is administered to the mammal orally, nasally, rectally, intravaginally, parenterally, buccally, sublingually, intragastrically or topically.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1D are a schematic illustration of compounds of the invention. FIG. 1A: Space-filling model of the D4 compound with the CVN component in blue, the linker in green, and the MPER component in white. FIG. 1B: Schematic hypothetical binding action of DAVEI on an HIV-1 envelope spike complex. FIG. 1C: Sequence of the D4 plasmid (nucleotide sequence SEQ ID NO:32; peptide sequence SEQ ID NO:33). SEQ ID NO:32 has the sequence of SEQ ID NO:30-SEQ ID NO:29 (pelB)-SEQ ID NO:2 (cyanovirin-N)-[(SEQ ID NO:34) (SEQ ID NO:6)$_4$]-SEQ ID NO:19 (His$_6$ tag)-SEQ ID NO:4 (MPER)-SEQ ID NO:31. The construct thus comprises the pelB signaling sequence, the CVN sequence, a flexible linker, a immobilized metal affinity purification tag, and MPER, which is followed by three ochre stop codons to stop protein translation. FIG. 1D: SDS PAGE gel electrophoresis demonstrating that the produced protein is >95% pure.

FIG. 2A: Inhibition of HIV-1 viral infection by D4 and D8 compounds. HOS.T4.R5 cells were exposed to BaL pseudotyped virus incubated with serial dilutions of the inhibitor compounds D8, D4, MPER, CVN, and a 1:1 CVN:MPER mixture. The % infected cells versus concentration of D8, D4, MPER, CVN, and CVN:MPER in pre-infection incubation were plotted and fit to a sigmoidal curve (mean±SD, n=3). EC$_{50}$s were calculated using Origin v. 8.1. FIG. 2B: Specificity controls for DAVEI inhibition of viral infection to HIV-1 envelopes. HOS.T4.R5 cells were exposed to VSV and A-MLV pseudotyped viruses incubated with serial dilutions of the compounds CVN, D4, D8 and MPER. The % infected cells vs. concentration of D4, D8, and 1:1 mixture of MPER and CVN in pre-infection incubation were plotted and fit to a sigmoidal curve (mean±SD, n=3).

FIG. 3 is a graph illustrating assessment of cell toxicity of HOS-T4-R5 cells in the presence of D4, D8, MPER and CVN. Assays used WST-1 reagent to determine viability of treated cells. No statistically significant differences were measured with vs. without reagents, p <<0.05, n=3 using a t test.

FIG. 4A: Release of p24 from HIV-1 BaL pseudotyped viruses upon incubation with D4, D8, MPER, CVN, and a 1:1 CVN:MPER mixture. FIG. 4B: Assessment of p24 release from control viruses by DAVEI compounds. Viruses pseudotyped with VSV and A-MLV envelopes were exposed to D4, D8 and 1:1 CVN:MPER. A sandwich ELISA assay was carried out in which experimental p24 release was background subtracted using PBS-treated virus and then compared to virus lysed with 1% Triton X-100 (mean±SD, n=3). IC$_{50}$s for D4 and D8 virolysis HIV-1 BaL pseudovirus were determined with Origin v. 8.1 to be 14.25±0.8 nM and 7.53±0.4 nM, respectively (mean±SD, n=3).

FIGS. 7A-7C are a set of TEM micrographs and graphs illustrating physical morphology of the D4- and D8-treated virions compared to virus treated with PBS ("Intact Virus"). The compounds were incubated with the HIV-1 BaL pseudovirus for 30 min at 37° C. before fixing the virions with 0.1% paraformaldehyde and loaded onto a holey carbon 200 mesh grid for TEM analysis. The grids were stained with 1% uranyl acetate and loaded onto a JEM 2100 microscope system (JEOL, Japan) operated at 120 kV. Energy-dispersive X-ray (EDX) spectroscopy was conducted on the sample (blue) and the empty mesh (red) in order to confirm assignment of virion particles. Spectroscopy results are shown on the right for the representative virion image in the upper left of each image set.

FIG. 8 is a schematic illustration of the construction of a MVN-DAVEI8 plasmid. For the MVN construct, the nucleotide sequence is SEQ ID NO:35, and the peptide sequence is SEQ ID NO:36.

FIG. 9 is a graph illustrating effects of cholesterol-depletion using MβCD on (i) lysis by 1 nM CVN-DAVEI8 (squares), (ii) infectivity by BaL.01 pseudovirus (circles), and (iii) infectivity by HIV-1 pseudotyped with VSV-G Env (triangles).

FIG. 10A: MVN, MVN-DAVEI4, and MVN-DAVEI8 on 15% SDS-PAGE gel. FIG. 10B: % Infectivity vs. ligand concentration for MVN (circles) and MVN-DAVEI-8 (squares). FIG. 10C: % p24 release vs ligand concentration for MVN-DAVEI-8 (circles; error bars are SD for n=3) and MVN (squares).

FIG. 11 illustrates distributions of WT and MVN-resistant (M) gp120 incorporation into Env trimers based on relative amounts of WT- and M-plasmids incorporated during virus production. The table reports % of each type of spike (W, W2M, WM2, M) produced in each case.

FIG. 12 illustrates docking of MVN-DAVEI8 to BG505-SOSIP.664 N295 glycan (modeled; top: stick representation). Top: Close-up of two major docking poses each comprising 100 samples from a separate MD simulations of MVN-DAVEI8. Bottom: Side view showing the full set of docked poses.

FIGS. 13A-13C illustrate the UM15-DAVEI4 construct. FIG. 13A: Structure of the UM15-DAVEI4 construct. The original UM15 peptide is shown on the top, the $(G_4S)_4$ linker in the middle, and the MPER peptide at the bottom. FIG. 13B: Infectivity vs. ligand concentration for UM15-DAVEI4, linker(4)-MPER and UM15 alone. FIG. 13C: % p24 release vs. concentration of UM15, UM15-DAVEI4, and the linker-MPER construct. Error bars in FIGS. 13B-13C indicate standard deviations (n=3).

DETAILED DESCRIPTION OF THE INVENTION

Figure 1A:
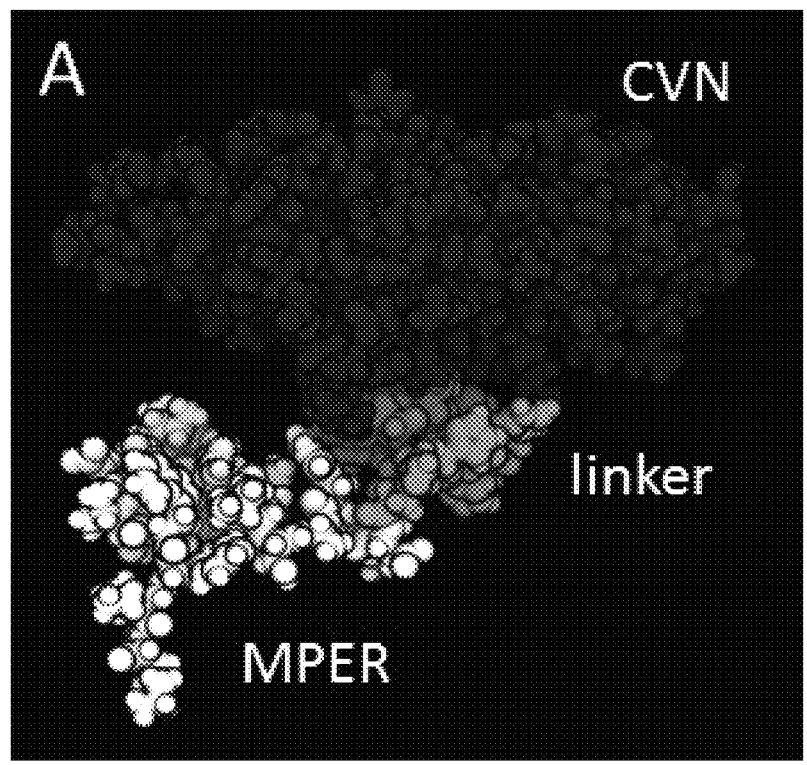
Figure 1B:
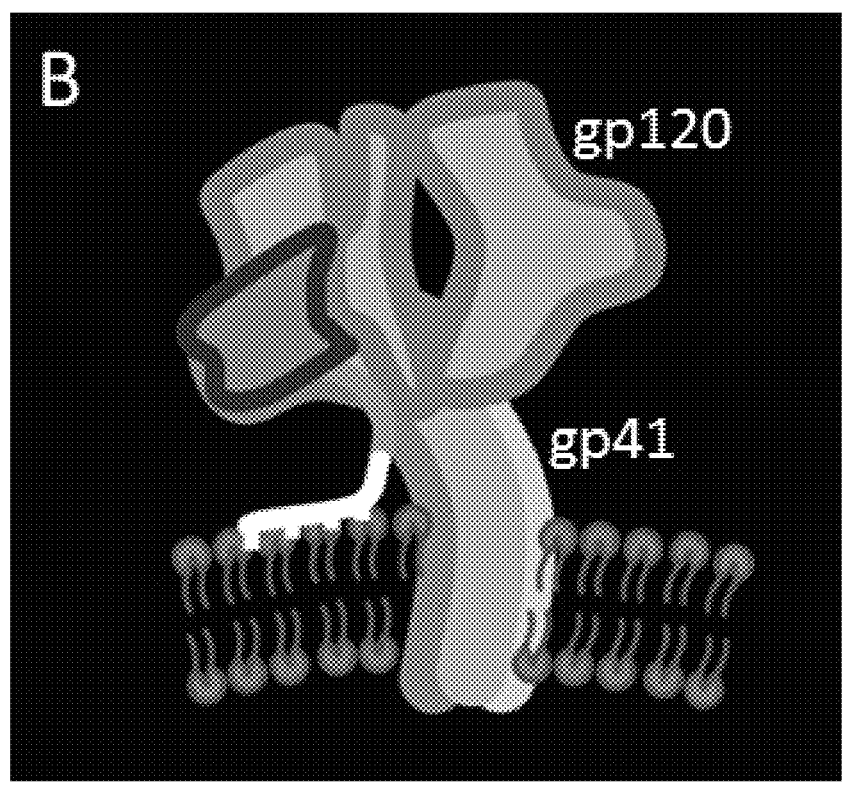

The present invention relates to the unexpected discovery of a novel class of compounds that prevent or treat HIV-1 infection. In certain embodiments, the compounds of the invention irreversibly destroy an HIV-1 virion by simultaneously binding to the virus Env protein and envelope membrane of the virion. In other embodiments, the HIV-virion is within the body of a mammal. The present invention further relates to a method of preventing or treating an HIV-1 infection in a mammal in need thereof, wherein the method comprises administering to the mammal a therapeutically effective amount of at least one compound of the invention, which is optionally formulated as a pharmaceutical composition.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration and the like, the term "about" is meant to encompass variations of ±20%, more preferably ±10%, more preferably ±5%, even more preferably ±1%, and still more preferably ±0.1% from the specified value, as such variations are appropriate to perform the disclosed methods.

As used herein, the term "AIDS" refers to acquired immunodeficiency syndrome.

As used herein, the term "antiviral agent" means a compound and/or composition that, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir®, Glaxosmithkline, Middlesex, UK) is an antiviral agent that is thought to prevent replication of HIV in human cells.

"Applicator" as the term is used herein is used to identify any device including, but not limited to, a hypodermic syringe, a pipette, and the like, for administering the compounds and compositions used in the practice of the invention.

As used herein with respect to the compounds of the invention, "biologically active" means that the compounds elicit a biological response in a mammal that can be monitored and characterized in comparison with an untreated mammal. One possible biological response within the invention relates to the ability of the compound to avoid, reduce or treat HIV-1 infection in a mammal. In this particular case, the compound is administered to the mammal orally, nasally, rectally, intravaginally, parenterally, buccally, sublingually, intragastrically or topically. The mammal and the HIV-1 viral load level in its body are monitored as a function of time, and the observation of a measurable and dose-dependent change in HIV-1 infection rate or viral load in the body is evidence that the compound displays biological activity. This preferred biological response does not limit or restrict the disclosures or embodiments of the invention in any way.

As used herein, the term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating or preventing HIV infection in a mammal.

As used herein, the term "CVN" refers to cyanovirin-N (SEQ ID NO:1 for peptide sequence; SEQ ID NO:2 for nucleotide sequence), or a salt or solvate thereof.

As used herein, the term "D4" refers to DAVEI 4 (also known as DAVEI4) or the sequence SEQ ID NO:1-(SEQ ID NO:6)$_4$-SEQ ID NO:5-SEQ ID NO:11, or a salt or solvate thereof.

As used herein, the term "D8" refers to DAVEI 8 (also known as DAVEI8) or the sequence SEQ ID NO:1-(SEQ ID NO:6)$_8$-SEQ ID NO:5-SEQ ID NO:11, or a salt or solvate thereof.

As used herein, the term "DAVEI" refers to dual acting virucidal entry inhibitor.

As used herein, the language "effective amount" or "therapeutically effective amount" refers to a non-toxic but sufficient amount of the composition used in the practice of the invention that is effective to treat, prevent or ameliorate HIV-1 infection in the body of a mammal. The desired treatment may be prophylactic and/or therapeutic. That result may be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, the term "Env" refers to a HIV-1 envelope protein spike.

As used herein, the term "HIV" refers to human immunodeficiency virus.

As used herein, the term "HIV-1" refers to human immunodeficiency virus type 1.

As used herein, the term "linker" refers to a chemical group, comprising one or more atoms, that covalently connects two or more chemical groups. In certain embodiments, the linker comprises a peptide. In other embodiments, the linker comprises an ethylene glycol oligomer. In yet other embodiments, the linker comprises an ethylene glycol oligomer and a peptide.

As used herein, the term "microvirin" refers to the peptide of SEQ ID NO:12, or a salt or solvate thereof.

As used herein, the term "MPER" refers to membrane proximal external region.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a $NH_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

As used herein, "natural amino acids" are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", $3^{rd}$ Ed., W. H. Freeman and Co., New York.

| Full Name | Three-Letter Code | One-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, a "pharmaceutically acceptable carrier" means a pharmaceutically acceptable material, composition or carrier, such as a liquid or solid filler, diluent, excipient, solvent or encapsulating material, involved in carrying or transporting compound(s) of the present invention within or to the subject such that it may perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; gar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; anti-oxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, the term "PT" refers to peptide triazole.

As used herein, the term "SPPS" refers to solid-phase protein synthesis.

As used herein, a "subject" or a "mammal" includes a human or a non-human mammal. Non-human mammals include, for example, livestock and pets, such as ovine, bovine, porcine, canine, feline and murine mammals. Preferably, the subject or mammal is human.

As used herein, a "therapeutic" treatment is a treatment administered to a subject who exhibits signs of pathology of a disease or disorder for the purpose of diminishing or eliminating those signs.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "VSV" refers to vesicular stomatitis virus.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Description

The invention relates to a novel class of compounds that prevent or treat HIV-1 infection in a mammal. In certain embodiments, the compounds of the invention irreversibly destroy an HIV-1 virion by simultaneously binding to the virus Env protein and viral membrane.

One way to permanently inactivate a virus is to induce poration of its membrane, resulting in the irreversible release of its cargo to the extracellular milieu where it is broken down. In one aspect, the viral spike and surrounding membrane in mature HIV-1 exist in a metastable state, and the natural downhill process of relaxing this metastability (which is possibly a driving force for fusion) may cause viral membrane poration in the absence of an apposing membrane. In another aspect, a molecule that binds to gp120 and simultaneously inserts into the viral membrane near the spike may impart stress to the spike, catalyzing relaxation of the metastability and consequently viral poration.

As described herein, a chimera was designed and prepared by fusing the lectin cyanovirin-N(CVN) to the 20-residue-long amphipathic peptide derived from the membrane proximal external region (MPER) of gp41 using a flexible polypeptide linker. CVN broadly inactivates HIV-1 and is microbicidal in its own right. CVN binds to carbohydrates on gp120, which, in the context of trimeric spike, prevents the binding of gp120 to CD4 but does not induce poration of virus. MPER alone partitions readily into model liposomal bilayers and likely orients itself as an amphipathic kinked helix that inserts its hydrophobic side chains into the ectoplasmic leaflet lipid chains. In a non-limiting embodiment, when such a fusion is exposed to the spike, the CVN component binds gp120 and the MPER-derived component inserts itself into the viral membrane near the spike.

As described herein, two chimeric fusions, named Dual Acting Virucidal Entry Inhibitor (DAVEI) compounds, were designed, recombinantly produced and characterized. These novel compounds were found to bind gp120 in soluble form in a manner similar to that of CVN alone. These chimeras were also able to block HIV-1 infection in a viral infection assay in low nanomolar concentrations. The antiviral activity was HIV-1 specific, as demonstrated by the fact that it did not inhibit VSV cell infection. Importantly, the chimeric proteins were found to release intraviral p24 from BaL pseudotyped HIV-1 in a dose-dependent manner in the absence of host cells. When viral stocks were treated with the DAVEI compounds alone, in the absence of target cells, virolysis occurs in a dose-dependent fashion with a low nanomolar $IC_{50}$. CVN and MPER each competed out the DAVEI virolytic function, indicating that both components of the fusion were required. In certain embodiments, this new class of dual-acting virucidal molecules irreversibly destroys the HIV-1 virion by simultaneously binds the virus Env protein and viral membrane.

Without wishing to be limited by any theory, the finding that engaging the Env protein spike and membrane using a chimeric ligand can destabilize the virus and lead to inactivation allows for exploration of virus particle meta-stability as a means of virus inactivation at the earliest stages of viral exposure and before host cell encounter. The compounds of the present invention may, in a non-limiting example, be used in microbicide preparations to prevent or treat HIV infections.

Compounds

The invention includes a compound of formula (I), or a salt or solvate thereof:

BINDER-LINKER-(SEQ ID NO:3) (I), wherein in (I) the BINDER binds to gp120; and the LINKER is a linker that covalently connects the C-terminus of the BINDER and the N-terminus of SEQ ID NO:3.

In certain embodiments, the BINDER comprises SEQ ID NO:1 or SEQ ID NO:12.

In certain embodiments, the BINDER comprises at least one sequence selected from the group consisting of the sequence $X_1X_2X_3NIXWX_4$ (III; SEQ ID NO:22), wherein in (III) $X_1$ is absent or E, $X_2$ is selected from the group consisting of F, K, E, R and Cit, $X_3$ is N or I, $X_4$ is S or T;

SEQ ID NO:23 (RINNIXW), SEQ ID NO:24 (INNIXW), SEQ ID NO:25 (NNIXWS), SEQ ID NO:26 (INIXWS) and SEQ ID NO:27 (NNIXW), wherein X is the modified proline of formula (IV):

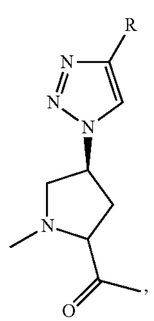

wherein in (IV) R is selected from the group consisting of naphthyl, p-methyl phenyl, p-ethyl phenyl, 2-phenylethyl and metallocene. In certain embodiments, the metallocene is ferrocene.

In certain embodiments, the LINKER is a linker that covalently connects the N-terminus of SEQ ID NO:3 and the C-terminus of a sequence selected from the group consisting of SEQ ID NOs:1, 12 and 22-27.

In certain embodiments, SEQ ID NO:3 comprises SEQ ID NO:11. In other embodiments, SEQ ID NO:3 consists of SEQ ID NO:11.

In certain embodiments, SEQ ID NO:3 comprises SEQ ID NO:21. In other embodiments, SEQ ID NO:3 consists of SEQ ID NO:21.

In certain embodiments, the LINKER comprises $(CH_2CH_2O)_x$, wherein 'x' is an integer ranging from 1 to 60. In other embodiments, 'x' is an integer ranging from 5 to 50. In yet other embodiments, 'x' is an integer ranging from 10 to 50.

In certain embodiments, the LINKER comprises a peptide of formula (II), or a salt or solvate thereof:

LINKER1-(LINKER2)$_n$ (II), wherein the LINKER1 comprises 1 to 60 amino acids; LINKER 2 comprises (H is)$_6$ (SEQ ID NO:5) or AspTyrLysAspAspAspAspLys (SEQ ID NO:9); and n is 0 or 1. In certain embodiments, the N-terminus of LINKER1 is covalently connected to the C-terminus of the BINDER in (I).

In certain embodiments, the LINKER1 consists of 1 to 60 amino acids. In other embodiments, the LINKER1 consists of 2 to 50 amino acids. In yet other embodiments, the LINKER1 consists of 5 to 50 amino acids. In yet other embodiments, the LINKER1 consists of 10 to 50 amino acids. In yet other embodiments, the LINKER1 comprises neutral amino acids. In yet other embodiments, the LINKER1 consists of neutral amino acids. In yet other embodiments, the LINKER1 comprises amino acids selected from the group consisting of glycine and serine. In yet other embodiments, the LINKER1 consists of amino acids selected from the group consisting of glycine and serine. In yet other embodiments, the LINKER1 consists of 10 to 50 neutral amino acids selected from the group consisting of glycine and serine.

In certain embodiments, the LINKER1 comprises 2 to 10 repeating units of a pentapeptide consisting of neutral amino acid residues. In other embodiments, the LINKER1 comprises 2 to 10 repeating units of a pentapeptide consisting of glycine and serine residues. In yet other embodiments, the LINKER1 consists of 2 to 10 repeating units of a pentapeptide consisting of glycine and serine residues.

In certain embodiments, the LINKER1 comprises (SEQ ID NO:6)$_m$ or (SEQ ID NO:10)-(SEQ ID NO:6)$_m$ (wherein $Gly_4Ser$=SEQ ID NO:6; $His_6$=SEQ ID NO:5; GlySer=SEQ ID NO:10), wherein 'm' is an integer ranging from 2 to 10. In other embodiments, the LINKER1 comprises (SEQ ID NO:6)$_m$ or (SEQ ID NO:10)-(SEQ ID NO:6)$_m$, wherein 'm' is an integer ranging from 4 to 8.

In certain embodiments, the LINKER1 comprises (SEQ ID NO:6)$_4$ or (SEQ ID NO:10)-(SEQ ID NO:6)$_4$. In yet other embodiments, the LINKER1 consists of (SEQ ID NO:6)$_4$ or (SEQ ID NO:10)-(SEQ ID NO:6)$_4$.

In certain embodiments, the LINKER1 comprises (SEQ ID NO:6)$_8$, (SEQ ID NO:10)-(SEQ ID NO:6)$_8$ or Ser-(SEQ ID NO:6)$_2$-Gly-(SEQ ID NO:6)-Gly-(SEQ ID NO:6)$_5$. In yet other embodiments, the LINKER1 consists of (SEQ ID NO:6)$_8$, (SEQ ID NO:10)-(SEQ ID NO:6)$_8$ or Ser-(SEQ ID NO:6)$_2$-Gly-(SEQ ID NO:6)-Gly-(SEQ ID NO:6)$_5$.

In certain embodiments, the LINKER comprises (SEQ ID NO:6)$_4$ or (SEQ ID NO:10)-(SEQ ID NO:6)$_4$. In other embodiments, the LINKER comprises (SEQ ID NO:6)$_4$-(SEQ ID NO:5) or (SEQ ID NO:10)-(SEQ ID NO:6)$_4$-(SEQ ID NO:5). In yet other embodiments, the LINKER comprises (SEQ ID NO:6)$_4$-(SEQ ID NO:9) or (SEQ ID NO:10) (SEQ ID NO:6)$_4$-(SEQ ID NO:9).

In certain embodiments, the LINKER comprises (SEQ ID NO:6)$_8$, (SEQ ID NO:10)-(SEQ ID NO:6)$_8$ or Ser-(SEQ ID NO:6)$_2$-Gly-(SEQ ID NO:6)-Gly-(SEQ ID NO:6)$_5$. In other embodiments, LINKER comprises (SEQ ID NO:6)$_8$-(SEQ ID NO:5), (SEQ ID NO:10) (SEQ ID NO:6)$_8$-(SEQ ID NO:5) or Ser-(SEQ ID NO:6)$_2$-Gly-(SEQ ID NO:6)-Gly-(SEQ ID NO:6)$_5$-(SEQ ID NO:5). In yet other embodiments, the LINKER comprises (SEQ ID NO:6)$_8$-(SEQ ID NO:9), (SEQ ID NO:10)-(SEQ ID NO:6)$_8$-(SEQ ID NO:9) or Ser-(SEQ ID NO:6)$_2$-Gly-(SEQ ID NO:6)-Gly-(SEQ ID NO:6)$_5$-(SEQ ID NO:9).

In certain embodiments, the compound of formula (I) comprises a peptide selected from the group consisting of:

SEQ ID NO:1-(SEQ ID NO:10)$_{0-1}$-(SEQ ID NO:6)$_4$-SEQ ID NO:5-SEQ ID NO:3;

SEQ ID NO:1-(SEQ ID NO:10)$_{0-1}$-(SEQ ID NO:6)$_4$-SEQ ID NO:3;

SEQ ID NO:1-(SEQ ID NO:10)$_{0-1}$-(SEQ ID NO:6)$_8$-SEQ ID NO:5-SEQ ID NO:3;

SEQ ID NO:1-(SEQ ID NO:10)$_{0-1}$-(SEQ ID NO:6)$_8$-SEQ ID NO:3;

SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:3;

SEQ ID NO:1-Ser-(SEQ ID NO:6)$_2$-Gly-(SEQ ID NO:6)-Gly-(SEQ ID NO:6)$_5$-SEQ ID NO:3;
SEQ ID NO:12-(SEQ ID NO:10)$_{0-1}$-(SEQ ID NO:6)$_4$-SEQ ID NO:5-SEQ ID NO:3;
SEQ ID NO:12-(SEQ ID NO:10)$_{0-1}$-(SEQ ID NO:6)$_4$-SEQ ID NO:3;
SEQ ID NO:12-(SEQ ID NO:10)$_{0-1}$-(SEQ ID NO:6)$_8$-SEQ ID NO:5-SEQ ID NO:3;
SEQ ID NO:12-(SEQ ID NO:10)$_{0-1}$-(SEQ ID NO:6)$_8$-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:3;
and combinations thereof.

In certain embodiments, the compound of formula (I) comprises a peptide selected from the group consisting of:
SEQ ID NO:1-(SEQ ID NO:10)$_{0-1}$-(SEQ ID NO:6)$_4$-SEQ ID NO:5-SEQ ID NO:11;
SEQ ID NO:1-(SEQ ID NO:10)$_{0-1}$-(SEQ ID NO:6)$_4$-SEQ ID NO:11;
SEQ ID NO:1-(SEQ ID NO:10)$_{0-1}$-(SEQ ID NO:6)$_8$-SEQ ID NO:5-SEQ ID NO:11;
SEQ ID NO:1-(SEQ ID NO:10)$_{0-1}$-(SEQ ID NO:6)$_8$-SEQ ID NO:11;
SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:11;
SEQ ID NO:1-Ser-(SEQ ID NO:6)$_2$-Gly-(SEQ ID NO:6)-Gly-(SEQ ID NO:6)$_5$-SEQ ID NO:11;
SEQ ID NO:12-(SEQ ID NO:10)$_{0-1}$-(SEQ ID NO:6)$_4$-SEQ ID NO:5-SEQ ID NO:11;
SEQ ID NO:12-(SEQ ID NO:10)$_{0-1}$-(SEQ ID NO:6)$_4$-SEQ ID NO:11;
SEQ ID NO:12-(SEQ ID NO:10)$_{0-1}$-(SEQ ID NO:6)$_8$-SEQ ID NO:5-SEQ ID NO:11;
SEQ ID NO:12-(SEQ ID NO:10)$_{0-1}$-(SEQ ID NO:6)$_8$-SEQ ID NO:11;
SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:11;
SEQ ID NO:12-Ser-(SEQ ID NO:6)$_2$-Gly-(SEQ ID NO:6)-Gly-(SEQ ID NO:6)$_5$-SEQ ID NO:11;
and combinations thereof.

Compositions

The invention includes a pharmaceutical composition comprising a compound of formula (I), or a salt or solvate thereof. In certain embodiments, the composition of the invention further includes at least one pharmaceutically acceptable carrier.

In certain embodiments, the composition further comprises at least one additional agent useful for treating HIV infections. In yet other embodiments, the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof.

Salts

The compounds described herein may form salts with acids or bases, and such salts are included in the present invention. In certain embodiments, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Methods

The invention also includes a method of promoting HIV-1 virolysis. The method comprises contacting HIV-1 with an effective amount of a compound comprising a compound of formula (I), or a salt or solvate thereof, thereby promoting HIV-1 virolysis. In certain embodiments, HIV-1 is present in the body of a mammal.

The invention further includes a method of preventing or treating an HIV-1 infection in a mammal in need thereof. The method comprises administering to the mammal a therapeutically effective amount of a compound of formula (I), or a salt or solvate thereof, whereby HIV-1 infection in the mammal is prevented or treated.

In certain embodiments, the mammal is further administered at least one additional agent useful for treating HIV infection. In other embodiments, the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof. In yet other embodiments, the at least one additional agent and the compound are co-formulated. In yet other embodiments, the at least one additional agent and the compound are co-administered. In yet other embodiments, the at least one additional agent and the compound are co-formulated and co-administered.

In certain embodiments, the compound is administered orally, nasally, rectally, intravaginally, parenterally, buccally, sublingually, intragastrically or topically to the mammal. In yet other embodiments, the mammal is human.

Combination Therapies

The compounds of the invention are useful in the methods of the invention in combination with one or more additional agents useful for treating HIV infections. These additional agents may comprise compounds or compositions identified herein, or compounds (e.g., commercially available compounds) known to treat, prevent, or reduce the symptoms of HIV infections.

In non-limiting examples, the compounds of the invention may be used in combination with one or more of the following anti-HIV drugs:

HIV Combination Drugs: efavirenz, emtricitabine or tenofovir disoproxil fumarate (Atripla®/BMS, Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

Entry and Fusion Inhibitors: maraviroc (Celsentri®, Selzentry®/Pfizer); pentafuside or enfuvirtide (Fuzeon®/Roche, Trimeris).

Integrase Inhibitors: raltegravir or MK-0518 (Isentress®/Merck).

Non-Nucleoside Reverse Transcriptase Inhibitors: delavirdine mesylate or delavirdine (Rescriptor®/Pfizer); nevirapine (Viramune®/Boehringer Ingelheim); stocrin or efavirenz (Sustiva®/BMS); etravirine (Intelence®/Tibotec).

Nucleoside Reverse Transcriptase Inhibitors: lamivudine or 3TC (Epivir®/GSK); FTC, emtricitabina or coviracil (Emtriva®/Gilead); abacavir (Ziagen®/GSK); zidovudina, ZDV, azidothymidine or AZT (Retrovir®/GSK); ddI, dideoxyinosine or didanosine (Videx®/BMS); abacavir sulfate plus lamivudine (Epzicom®/GSK); stavudine, d4T, or estavudina (Zerit®/BMS); tenofovir, PMPA prodrug, or tenofovir disoproxil fumarate (Viread®/Gilead).

Protease Inhibitors: amprenavir (Agenerase®/GSK, Vertex); atazanavir (Reyataz®/BMS); tipranavir (Aptivus®/Boehringer Ingelheim); darunavir (Prezist®/Tibotec); fosamprenavir (Telzir®, Lexiva®/GSK, Vertex); indinavir sulfate (Crixivan®/Merck); saquinavir mesylate (Invirase®/Roche); lopinavir or ritonavir (Kaletra®/Abbott); nelfinavir mesylate (Viracept®/Pfizer); ritonavir (Norvir®/Abbott).

A synergistic effect may be calculated, for example, using suitable methods such as, for example, the Sigmoid-$E_{max}$ equation (Holford & Scheiner, 19981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

Routes of administration of any of the compounds of the invention include oral, nasal, rectal, intravaginal, parenteral (e.g., IM, IV and SC), buccal, sublingual or topical. The regimen of administration may affect what constitutes an effective amount. The therapeutic formulations may be administered to the subject either prior to or after the onset of a viral infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compounds of the present invention to a subject, preferably a mammal, more preferably a human, may be carried out using known procedures, at dosages and for periods of time effective to treat a viral infection in the subject. An effective amount of the therapeutic compound necessary to achieve a therapeutic effect may vary according to factors such as the state of the disease or disorder in the subject; the age, sex, and weight of the subject; and the ability of the therapeutic compound to treat a viral infection in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound useful within the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compounds of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors, including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian may start doses of the compounds useful within the invention employed in the pharmaceutical composition at levels lower than that required in order to achieve the desired therapeutic effect and gradually increase the dosage until the desired effect is achieved.

In certain embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such a therapeutic compound for the treatment of an HIV-1 infection in a subject.

In certain embodiments, the compounds of the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compounds of the invention are administered to the subject in dosages that range from one to five times per day or more. In other embodiments, the compounds of the invention are administered to the subject in range of dosages that include, but are not limited to, once every day, every two, days, every three days to once a week, and once every two weeks. It is readily apparent to one skilled in the art that the frequency of administration of the various combination compounds of the invention varies from individual to individual depending on many factors including, but not limited to, age, disease or disorder to be treated, gender, overall health, and other factors. Thus, the invention should not be construed to be limited to any particular dosage regime and the precise dosage and compound to be administered to any subject are determined by the attending physical taking all other factors about the subject into account.

Compounds useful within the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound useful within the invention is from about 1 mg and about 2,500 mg. In some embodiments, a dose of a compound useful within the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., an HIV-1 antiviral) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

In certain embodiments, the present invention is directed to a packaged pharmaceutical composition comprising a container holding a therapeutically effective amount of a compound useful within the invention, alone or in combination with a second pharmaceutical agent; and instructions for using the compound to treat, prevent, or reduce one or more symptoms of an HIV-1 infection in a subject.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the invention, and a further layer providing for the immediate release of a medication for HIV-1 infection. Using a wax/pH-sensitive polymer mix, a gastric insoluble composition may be obtained in which the active ingredient is entrapped, ensuring its delayed release.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The compounds of the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intraarterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration:

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration:

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms:

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing:

The therapeutically effective amount or dose of a compound of the present invention will depend on the age, sex and weight of the subject, the current medical condition of the subject and the nature of the HIV-1 infection being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

All reagents were of analytical grade or better purchased from VWR. Modified human osterosarcoma cells (HOS.T4.R5), Amphotropic-Murine Leukemia Virus Env (A-MLV) and pNL4-3.Luc R-E- were gifts from Dr. Nathaniel Landau. The HIV-1 BaL plasmid was a gift from Dr. Julio Martin Garcia.

The Vesicular Stomatitis Virus Glycoprotein (VSV-G) plasmid was a gift from Dr. Lung-Ji Chang. Fully infectious HIV-1 BaL virions were a gift from the Center for AIDS Research at University of Pennsylvania. The WST-1 reagent was obtained from Takara Bio Inc.

23-mer MPER peptide and anti-MPER antibodies 2F5, 4E10 and Z13 were obtained from NIH AIDS Reagent Program, Division of AIDS, NIAID, NIH.

Polyclonal rabbit anti-CVN antibody was a gift from Biosyn, Inc. Uranyl acetate was obtained from Sigma-Aldrich and the lacey carbon 200 mesh copper grid was obtained from Pacific Grid Tech.

Plasmid Construction

DAVEI-4 (D4) and DAVEI-8 (D8) were successfully formed via a vector/cassette insertion strategy. Previous vectors containing L5 and L7 fusion proteins were sequenced (McFadden et al., 2007, Proteins 67:617-629), digested with HindIII and then BamH1 for 1-2 hours at 37° C., before being treated with Shrimp Alkaline Phosphatase (New England Biolabs) overnight at 37° C.

The vectors were then purified on a 1% agarose gel with a QIAQuick Gel Extraction kit (QIAGEN). PCR amplification of the cassette insert containing the internal His6 tag and MPER segment from HIV-1 BaL Env gene was accomplished using the 100 forward primer: TTTTGGATCCCATCAT-CATCATCATCATGACAAATGGGCAAGT (SEQ ID NO:7) and reverse primer: ATAATGAATAGAGTTAGG-TAAAAGTCCGGGT (SEQ ID NO:8) (IDT Tech). PCR amplification was done under standard conditions, and the product purified using a 1% agarose gel and the aforementioned gel extraction kit (QIAGEN). Ligation of the vector and cassette insert was carried out overnight, heat inactivated at 65° C., then transformed in XL-10 gold E. coli, plated on LB-Kan agar plates and grown for 16 hours at 37° C. Positive colonies were isolated and scaled up in 2-5 ml LB-Kan cultures and the DNA was isolated using a miniprep kit (QIAGEN). Automated DNA sequencing with T7 forward and reverse priming were used to confirm the correct DAVEI sequences for both D4 and D8.

Plasmid Construction

MVN-DAVEI4 and MVN-DAVEI8 plasmid were constructed using the vector/cassette insertion method (FIG. 8). CVN-DAVEI4 and CVN-DAVEI8 plasmids were sequenced, and BamH1 and Nde1 restriction sites were introduced using primers as follows: 5'-GGTGGAGGCGGGTCCCATCAT-CATCATCATC-3' (SEQ ID NO:13) and its complement to remove old BamH1 site; 5'-GAAGGAGATATACACAT-GAAATACCTGCTGC-3'(SEQ ID NO:14) and its complement to remove old Nde1 site; 5'-CCAGCCGGCGATG-CATATGGGTAAATTCTCC-3'(SEQ ID NO:15), and its complement to introduce new Nde1 site; 5'-GGTACCCT-GAAATACGAAGGATCCGGTGGCGGAGG-3' (SEQ ID NO:16), and its complement to introduce New BamH1 site.

The plasmids were digested to remove the cyanovirin (CVN) coding gene. Same restriction sites were introduced in Microvirin (MVN) containing pET15b plasmid using primers as follows: 5'-CCAACTGGAAATTGGATCCGATCCG-GCTGCTAAC-3'(SEQ ID NO:17), and its complement to introduce new BamH1 site; 5'-GGTGCCGCGCGGC-CATATGCCTAATTTTTCGCAC-3' (SEQ ID NO:18), and its complement to introduce new Nde1 site.

Plasmids were digested with BamH1 and Nde1 for 2 hours at 37° C. Digested plasmids were loaded on 1% agarose gel and cut vectors as well as inserts were isolated using QIA quick gel extraction kit. Ligation of the vector and MVN containing insert was carried out overnight (1:3 ratio). The plasmids were transformed into XL10 Gold competent cells, plated on agar plates (Kanamycin resistant) and incubated at 37° C. for 16 hours. Kanamycin resistant colonies were selected from the agar plates, inoculated at 10 mL LB media culture containing Kanamycin. Plasmids were extracted using Standard Miniprep protocol (Qiagen). The protein fusion was confirmed via DNA sequencing using T7 promoter (Genewiz).

Purification Protocol:

The MVN-DAVEI4 and MVN-DAVEI8 plasmids were transformed into BL21(DE3)pLys cells and plated on Kanamycin resistant plates. The plate was incubated overnight at 37° C. Kanamycin resistant colonies were picked next day and inoculated in 1 L LB media for 4 hours at 37° C. After 4 hours, cells were induced with IPTG and inoculated for 8 hours at 37° C. Cells were harvested after 8 hours, lysed via sonication, centrifuged, and protein containing supernatant was loaded onto Ni-NTA column. The bound protein was eluted with Imidazole gradient. Protein was dialyzed on 1×PBS and concentrated protein was loaded onto 20/60 Superdex 200 column using AKTA FPLC system. Fraction containing protein was ran on 15% gel (FIG. 10A), pooled together and flash frozen at −80° C. Protein concentration was determined by measuring absorbance at 280 nm wavelength. Purified fusion protein (MVN-DAVEI8) exhibited both antiviral and virolytic properties, whereas recombinant microvirin (SEQ ID NO:12) only exhibited antiviral property (FIGS. 10B-10C).

Protein Expression and Purification

The DAVEI and CVN plasmids were transformed into BL21(DE3)pLysS cells and scaled up in both LB and Super-broth media in 0.5 L cultures using kanamycin (for DAVEI protein selection) and chloramphenicol (for BL21(DE3) pLysS cell selection) at 37° C. Protein expression was induced using 1 mM ITPG for 8-10 hours at 30° C. In order to perform extraction of periplasmic proteins from the bacterial membrane, the cell suspension was pelleted and lysed before being sonicated using a microtip probe (Misonix 3000). The sonicated sample was spun down for 30 minutes at 10,000×g to separate the bacterial debris from the protein-containing supernatant. The protein was then purified by gravity flow affinity capture with NiNTA beads (QIAGEN) followed by gel filtration with a 26/60 Superdex 200 prep grade (GE Healthcare) column using an ATKA FPLC (GE Healthcare). Western blots of the NiNTA and gel filtration elution fractions combined with ELISA analyses were used to track protein content in eluates. Fractions containing target proteins were concentrated and buffer-exchanged to phosphate-buffered saline at pH 7.4 using a 5,000 MWCO spin filter (Amicon). The final protein was examined on a 15% SDS-PAGE gel and subsequent Coomassie blue and silver staining. Western blot analysis with rabbit anti-CVN was used to confirm the presence of the CVN component, and MPER antibodies 2F5, 4E10 and Z13e1 were used to confirm the MPER component of the DAVEI compounds. The final concentration was determined using absorbance at 280 nm and an extinction coefficient at 280 nm of 39,740 $M^{-1}$ $cm^{-1}$.

Cyanovirin-N and gp120 were produced in E. coli and CHO (Chinese Hamster Ovary) cells, respectively, as reported in McFadden et al., 2007, Proteins-Struct. Funct. Bioinf. 67:617-629; Cocklin et al., 2007, J. Virol. 81:3645-3648; Colleluori et al., 2005, Protein Expr. Purif. 39:229-236.

Production of BaL, VSV-G and A-MLV Pseudotyped Virus

The recombinant virus consisted of the pro-viral envelope plasmid sequence corresponding to the CCR5 targeting HIV-1 BaL strain and the backbone sequence corresponding to an envelope-deficient pNL4-3-Luc+Env provirus developed by Connor et al., 1995, Virology 206:935-944.

4 μg of envelope and 8 μg of backbone DNA were co-transfected into 293T cells using the transfection reagent FuGene 6 following the manufacturer's protocol (Montefiori, 2005, Curr. Protoc. Immunol. Chapter 12:Unit 12 11). 14 hours post-transfection the medium was changed, and the VLP containing media supernatants were collected 48 hours later. The VLP-containing supernatants were cleared of cell debris by low speed centrifugation, and filtered using a 0.45 μm syringe filter. Further, these VLP supernatants were purified by spinning the sample on a 6%-20% continuous Iodixanol gradient at 30,000 rpm for 2 hours at 4° C. using an SW41 rotor (BeckmanCoulter). The purified VLP samples were collected from the bottom fraction and stored at −80° C. until further use. The non-CD4/CCR5 targeting pseudotyped envelope Vesicular Stomatitis Virus (VSV) and Amphotropic Murine Leukemia Virus were produced following the same procedure as the HIV-1 BaL virus production and infectivity confirmed with HOS.T4.R5 cells.

Viral Inhibition and Cytotoxicity Assays

The following luciferase reporter assay system was used in order to monitor both the inhibition of HIV-1 infection by the DAVEI compounds and the extent of DAVEI cytotoxicity.

The infectious titer of the purified BaL pseudotyped virus was predetermined using the luciferase system, and the infectious dilution of the virus was pre-incubated with serial dilution of the DAVEI inhibitors for 30 minutes at 37° C. HOS.T4.R5 cells seeded at 8,000 cells per well were incubated at 37° C. for 24 hours followed by addition of the pre-incubated inhibitor-virus complex. The medium was changed 24 hours after addition of the complex. Forty eight hours post infection the cells were lysed by incubating with 50 μl of Passive Lysis Buffer (Promega) per well for 5 minutes followed by three freeze/thaw cycles. Luciferase assays were performed using 1 mM D-luciferin salt (Anaspec) as substrate and detected on a 1450 Microbeta Liquid Scintillation and Luminescence Counter (Wallac and Jet). Data from triplicate experiments were fit with non-linear regression analyses using Origin V.8.1 (Origin Lab), and $EC_{50}$ values were determined. Results were expressed as relative infection with respect to cells infected with virus in the absence of inhibitor (100% infected). Specificity of DAVEI compounds was assayed with VSV-G pseudotyped virus and the same protocol.

The DAVEI compounds, D4 and D8, as well as MPER and CVN were tested for cytotoxicity in vitro with HOS-T4-R5 cells. The latter were seeded at 8,000 cells per well and incubated with inhibitors as above in the infection inhibition assays. Cell viability was determined using the tetrazolium salt premix reagent WST-1 from Takara Bio Inc., following the manufacturer's protocol. The formazan product was measured 24 hours post-exposure using a microplate reader (Molecular Devices) at absorbance wavelength 450 nm.

Virolysis Assays

Serial dilutions of the DAVEI, MPER and CVN compounds were added for 30 minutes to a 1:4 working dilution of the HIV-1 BaL pseudotyped virus. The control samples included PBS with virus (negative lysis control) and 1% Triton X-100 with virus boiled for 5 minutes (positive lysis control). Following this incubation, the samples were spun for 2 hours at 13,200 rpm and 4° C. on a 5415R tabletop centrifuge (Eppendorf). The top 120 μL soluble fraction was collected and tested for p24 content using Western blot analysis (Bastian et al., 2011, ChemMedChem 6:1335-1339, 1318) and a sandwich capture ELISA as follows. High binding, polystyrene ELISA plates (Fisher Scientific) were coated overnight at 4° C. with 50 ng of mouse anti-p24 (Abcam) and blocked with 3% BSA. Following PBS-T rinsing (three times, five minutes each), the soluble fractions from the centrifuged DAVEI treated HIV-1 BaL samples were loaded using a 1:100 dilution factor with 0.5% BSA and incubated for 2 hours.

Soluble p24 in these fractions was detected using rabbit anti-p24 (Abcam) and anti-rabbit IgG-HRP (Invitrogen) at 1:5,000 dilution following the manufacturer's protocol. The ELISA plate was read on a transmission plate reader (Molecular Devices) using o-phenylenediamine dihydrochloride (OPD, Sigma) detection after 30 minute incubation at k=450 nm, and the PBS treated virus signals were subtracted. Signals were then plotted as a function of % of p24 released as compared to the fully lysed virus control treated with 1% Triton-X-100, boiled for five minutes. The data were fit using Origin V.8.1, to determine $IC_{50}$ values. This procedure was repeated with fully infectious HIV-1 BaL virions in a BSL-2 facility.

Competition Virolysis Assays

Serial dilutions of MPER and CVN were added to 50 nM DAVEI compounds and incubated for 30 minutes with a 1:4 working dilution of the purified BaL pseudovirus. The soluble fraction was separated and the virolysis assay was carried out with the same sandwich ELISA protocol as described elsewhere herein. Virus in PBS and 1% Trition X-100 followed by 5 minutes of boiling were the negative and positive controls, respectively. Data from triplicate signals were then plotted as a function of % of p24 released as compared to the positive control. The data were fit using Origin V.8.1, to determine $IC_{50}$.

TEM Analysis of DAVEI Treated Virions

Transmission electron microscopy (TEM) analysis was conducted to assess the morphology of untreated and D4- and D8-treated virions. Pseudotyped HIV-1 BaL was treated with D4 or D8 at 100 nM from 10 to 30 min at 37° C. The samples were then spun for 2 hours at 16,000 rpm in an ultracentrifuge (Eppendorf) at 4° C. The residual virions were fixed using 0.1% paraformaldehyde for 15 min at 4° C. The paraformaldehyde was filtered using a 100 kDa filter (Millipore), and the virions were resuspended in deionized water. The samples were then loaded onto a lacey carbon 200 mesh grid (Pacific Grid Tech), and the grid was then negatively stained using 2% uranyl acetate. Once the grid was dried, the samples were loaded onto a JEM 2100 microscope system (JEOL, Japan) operated at 120 kV. The virus images and the background mesh were evaluated by energy-dispersive X-ray spectroscopy (EDX) in order to confirm identification of virions. The uranium signal was used as a marker to confirm virions prior to imaging.

Example 1

A newly devised protein fusion of CVN and HIV-1 MPER peptide, termed DAVEI, was made using a prokaryotic recombinant expression system. DAVEI compounds have a $(Gly_4Ser)_x$-His6 (or (SEQ ID NO:6)$_4$-(SEQ ID NO:5)) linker between the CVN and MPER components (FIG. 1A). "D4" refers to DAVEI with x=4, and "D8" refers to DAVEI with x=8. Gene sequencing analysis confirmed the correct sequence for the CVN, linker, poly-histidine tag and MPER components in the constructed vector, as seen in the sequence in FIG. 1C for D4.

Using a combination of immobilized metal affinity chromatography and size-exclusion chromatography, the proteins were purified to >95% homogeneity as demonstrated by SDS-PAGE analysis (FIG. 1D). Typically, a 1 L culture yielded 5 ml of DAVEI at a concentration of roughly 3-5 µM.

ELISA and SPR screening assays were used to demonstrate that the D4 and D8 proteins were able to bind gp120. The linker appears to have no negative effects on the CVN binding capability because this portion of the fusion protein was easily detected with Western blots probed with anti-CVN. However, when either of the DAVEI constructs was probed with the MPER specific antibodies 4E10, 2F5 and Z13e1 in a Western blot assay, no signal was discernible. Since these antibodies are sensitive to MPER conformation and location (lipid-protein interface), they might not recognize MPER peptides in the Western blots.

Figures 2A, 2B:
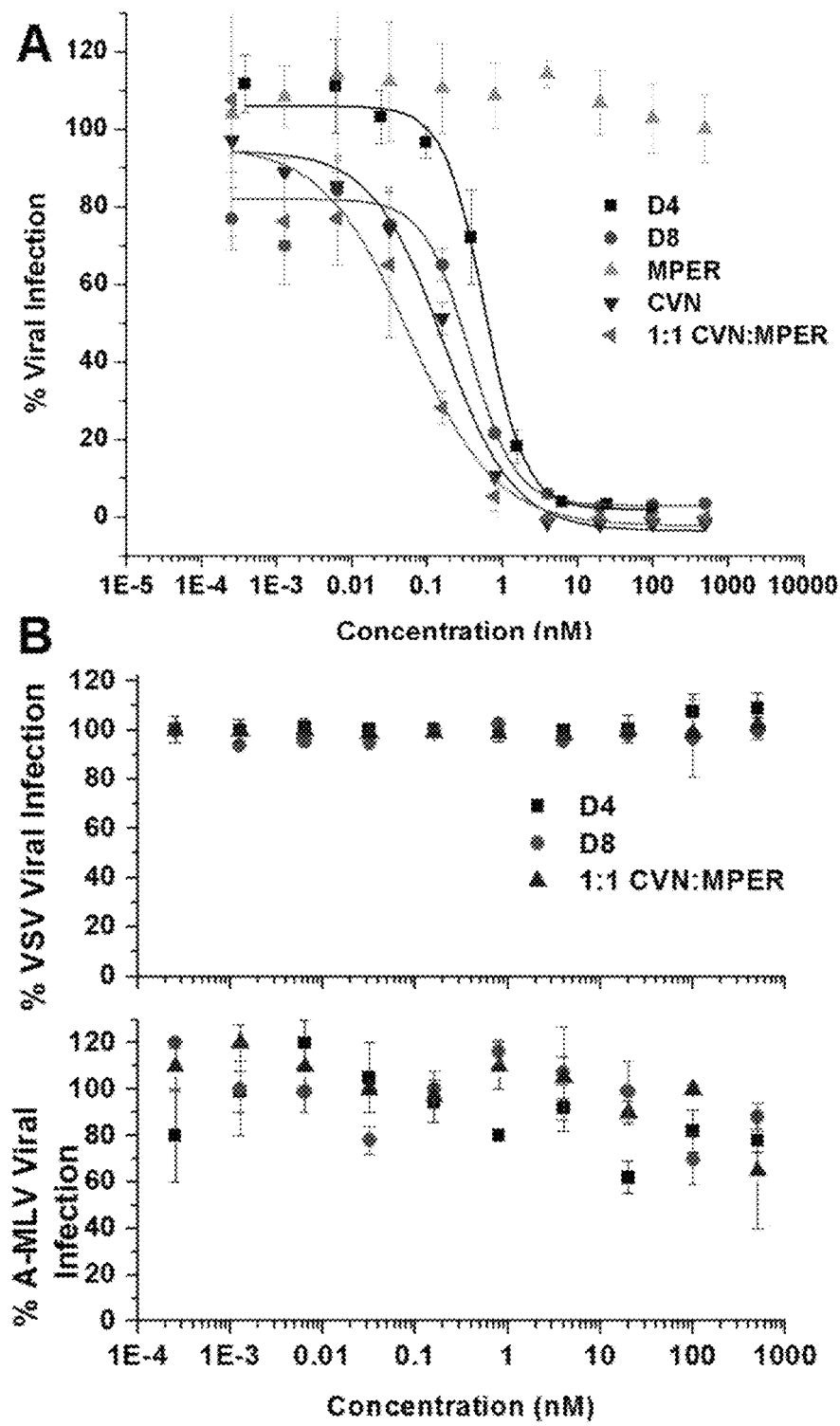
FIGS. 2A-2B are a set of graphs illustrating HIV-1 specific inhibition of cell infection by DAVEI compounds.

Experiments were then run to evaluate whether the chimerae had compromised infectivity inhibition relative to CVN. CVN and the chimeric fusions D4 and D8 had significant antiviral activity against HIV-1 BaL viral entry in a single-round infectivity assay, whereas MPER alone seemed devoid of inhibitory activity. As illustrated in FIG. 2A, data from triplicate experiments indicated that CVN, D4, D8, a 1:1 mixture of CVN and MPER peptide, and MPER peptide alone have $IC_{50}$ values of 0.16±0.031 nM, 0.58±0.069 nM, 0.36±0.12 nM, 205 0.6±0.3 nM, and >10 µM, respectively. D4 and D8, like CVN, acted specifically against HIV-1 Env. When these compounds were tested in an infection assay with pseudoviruses expressing the VSV or A-MLV envelope protein instead of HIV-1 Env, no significant dose-dependent viral entry inhibition (which in the case of VSV occurs via an endocytotic pathway) was observed (FIG. 2B). Hence, the CVN and chimeric fusions demonstrated specificity for virus displaying the HIV-1 210 envelope proteins.

The cytotoxicity of the DAVEI compounds was tested using the WST-1 reagent. HOS.T4.R5 cells were seeded at 8,000 cells per well in a 96 well plate. Post treatment with DAVEI compounds, the reagent was added following manufacturer's protocol. FIG. 3 shows that no significant cytotoxicity was observed either with the DAVEI compounds or with CVN and MPER alone at concentrations below 101.1M.

Figures 4A, 4B:
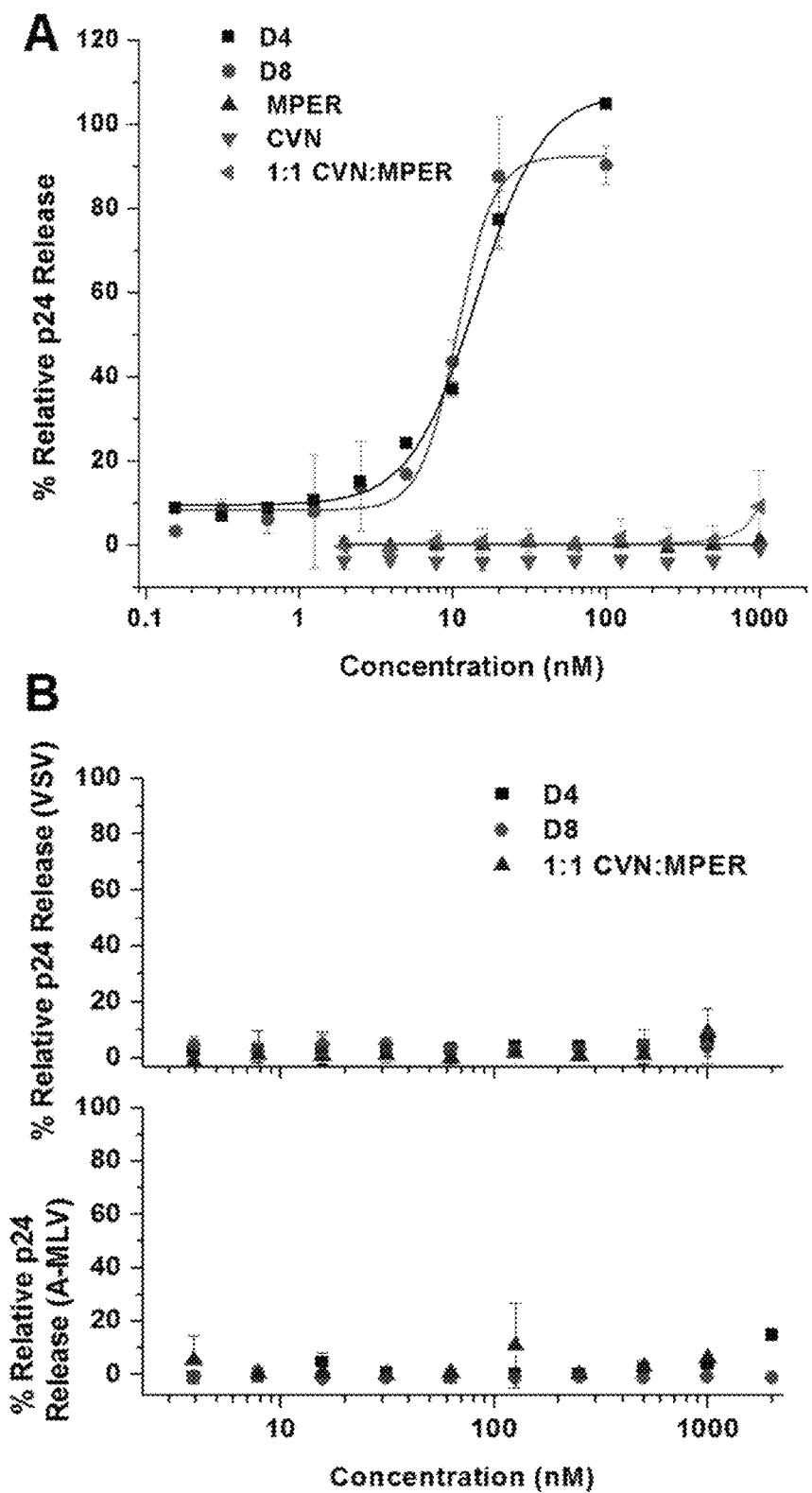
FIGS. 4A-4B are a set of graphs illustrating virolysis of HIV-1 by DAVEI fusions.

The ability of CVN, D4, D8 and MPER to cause leakage of the internal viral capsid protein p24 was tested. As illustrated in FIG. 4A, D4 and D8 have $IC_{50}$ values for viral leakage of 14.25±0.8 nM and 7.53±0.4 nM, respectively. Without wishing to be limited by any theory, because the positive lysis control was boiled for 5 minutes in 1% detergent solution, the 100% relative p24 leakage observed in the assay most likely reflects complete and irreversible destruction of the virus. Moreover, when CVN or the MPER peptide were added alone or in a 1:1 mixture, they were unable to induce the leakage of intraviral p24 at concentrations up to at least 10 µM (FIG. 4A). Finally, D4 and D8 induced no leakage in the VSV- and AMLV-envelope-presenting control viruses (FIG. 4B).

Figure 5:
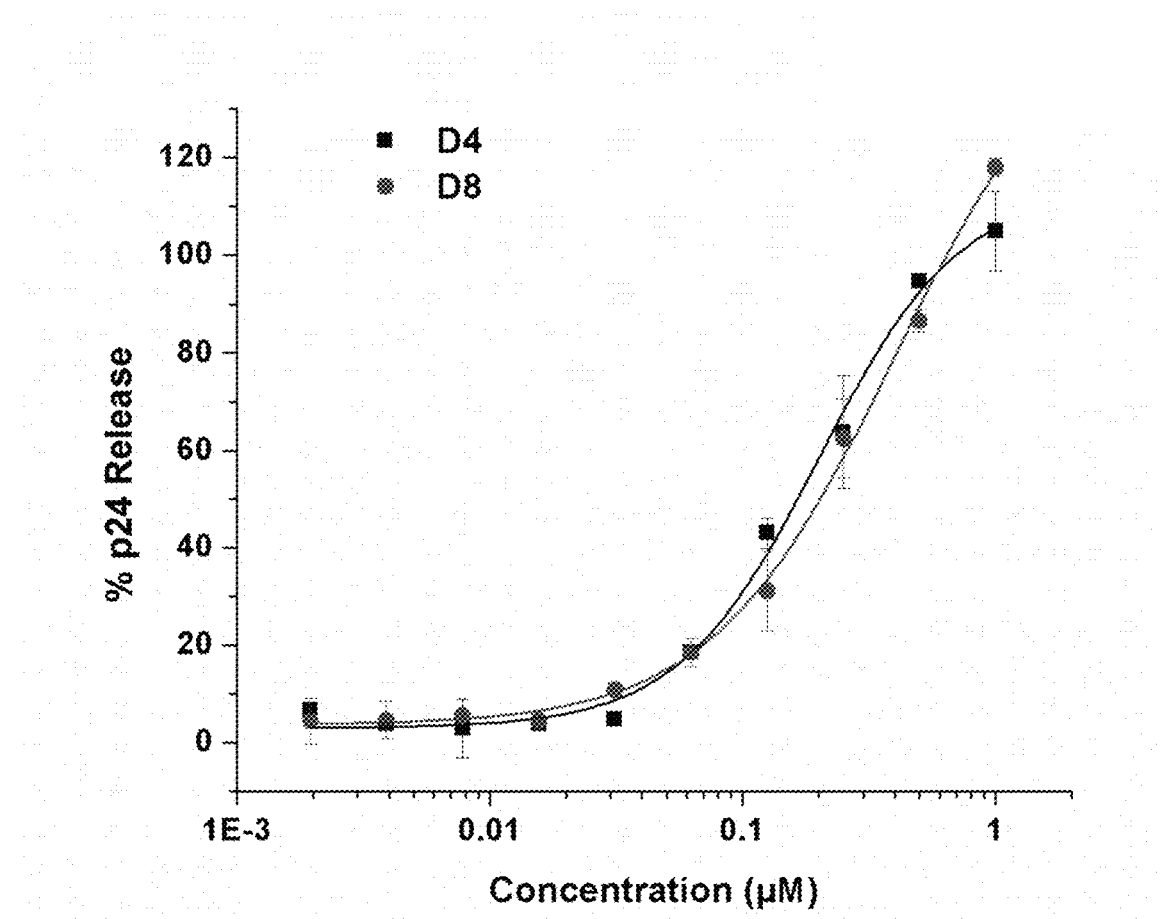
FIG. 5 is a graph illustrating virolysis of HIV-1 BaL fully infectious virus by D4 and D8. Release of p24 by D4 and D8 were tested with a p24 leakage assay using ELISA. The $IC_{50}$ values for D4 and D8 induced virolysis were 199.98±22 nM and 395.4±71.5 nM, respectively, determined using Origin Pro V.8.1 with sigmoidal fits (mean±SD, n=3).

Induction of p24 leakage by D4 and D8 was also tested with fully infectious HIV-1 BaL. FIG. 5 shows that both of the DAVEI compounds cause concentration dependent leakage of p24 from fully infectious HIV-1 BaL with $IC_{50}$ values of 199.98±22 nM and 395.4±71.5 nM for D4 and D8 respectively. These results demonstrate that the actions of DAVEI inhibitors are generally applicable to HIV-1 and not simply to pseudovirus constructs.

Figure 6A:
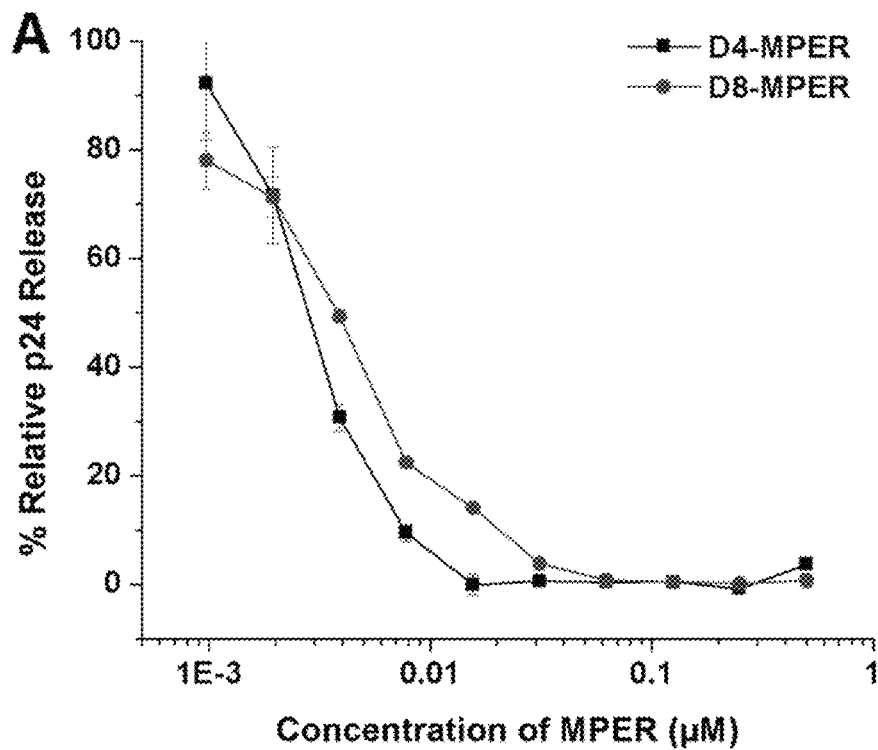
FIGS. 6A-6B are a set of graphs illustrating the requirement of both MPER and CVN components of DAVEI fusions for virus lysis. MPER (FIG. 6A) and CVN (FIG. 6B) competed out the inhibition of virolysis by D4 and D8, respectively. D4 and D8 concentration was 50 nM, and serial dilution of both MPER and CVN started from 0.5 µM. The relative p24 release was measured using p24 ELISA (mean±SD, n=3).
Figure 6B:
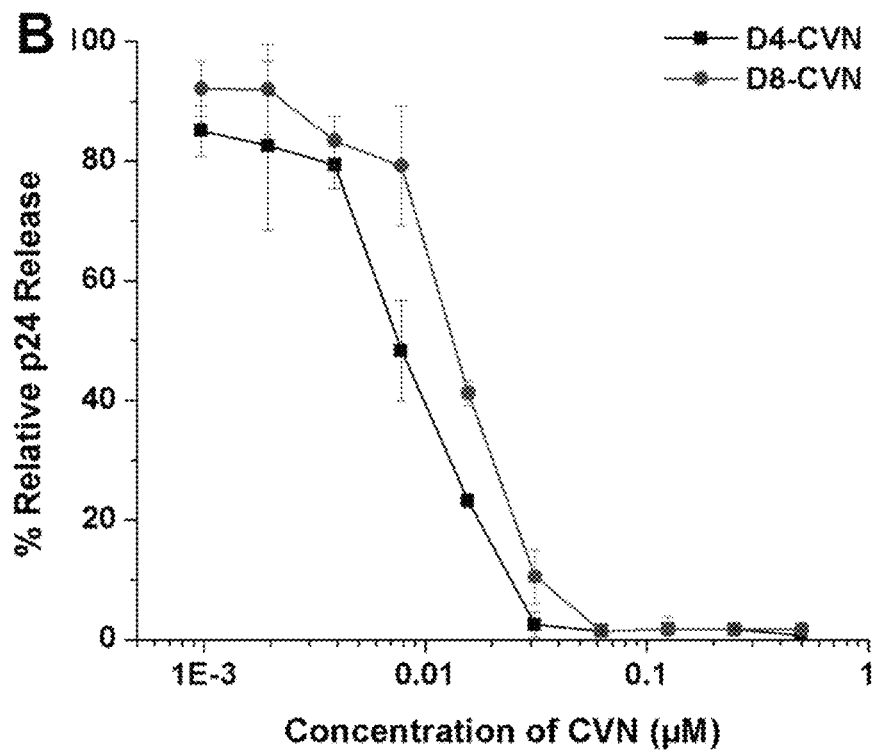

The question of whether both components of the fusion were required for virolysis was evaluated. Assays were performed to quantify the degree to which free MPER or free CVN competed out the virolytic activity of D4 and/or D8. CVN and MPER competition of the virolytic activity of both D4 and D8 was observed in a dose-dependent fashion, as illustrated in FIGS. 6A-6B, respectively. The concentrations at which free MPER began to compete out virolysis were very \low, with IC50's less than 10 nM for both D4 and D8, suggesting a specific, high-affinity site for exogenous MPER binding in viral membrane or on Env spike.

TEM analysis was conducted in order to study the structure of the virions post treatment with DAVEI compounds, D4 and D8, in comparison to the intact virus (PBS treated). FIGS. 7A-7C contains 8 images obtained using the TEM system for each treatment. These images showed that the DAVEI-treated virions show significant morphological differences relative to intact virions consistent with large-scale membrane disruption and content leakage. EDX analysis confirmed that the images obtained were of virion or virion-like particles and not background.

As discussed herein, the chimeric DAVEI fusions D4 and D8 induced specific, irreversible and inactivating lysis of pseudotyped HIV-1 virions, while being non-toxic to the host cells tested. Without wishing to be limited by any theory, the activity of DAVEI may be based on at least two elements: (i) the Env spike in a mature virus is metastable and, when triggered, can relax in a manner that porates the viral membrane in the absence of an apposing membrane; and (ii) a binder that imparts an external stress to the spike can trigger transformation of the metastable structure. In view of the data presented herein, the CVN component appeared to act like free CVN, binding the carbohydrates on the Env spike, and fusing it to MPER did not alter how it binds. Free exogenous MPER competed out DAVEI even at very low MPER concentrations (FIG. 6A), suggesting the presence of specific MPER binding sites on the viral membrane or at the spike/membrane junction or perhaps on the spike itself. In one non-limiting embodiment, these sites, if they exist, are mute with respect to virolysis when only free MPER binds, or, if they do not normally exist in Env spike, may be induced by CVN binding in a way akin to CD4 induction of the coreceptor site on gp120. Regardless of whether these putative exogenous MPER sites on the virus are persistent or induced, the competition data clearly indicated that a covalent linkage from the MPER to the CVN is important to trigger virolysis, as supported by the fact that simultaneous exposure of spike to a 1:1 mixture of MPER and CVN was not sufficient to induce virolysis.

Without wishing to be limited by any theory, in one non-limiting embodiment, the physical basis of the virolytic action may relate to the model wherein, when one or more DAVE1 molecules bind to a spike, they "tether" its gp120 components to the membrane, and that this tethering induces stress that catalyzes poration-inducing conformational changes in the spike or strain in the membrane close to the spike that results in irreversible poration. In another non-limiting embodiment, the CVN part of the fusion may bind to the spike gp120 of one virus, while the MPER portion binds to the membrane of another virus such that both viruses are lysed as they move apart by Brownian motion. It may be noted that multi-virion aggregates are not observed as a frequent occurrence in TEM imaging of D4- and D8-treated viruses.

In a non-limiting aspect, the results reported herein relate to the synthesis and characterization of novel virolytic compounds recombinantly constructed by fusing CVN and HIV-1 MPER peptide with flexible peptide linkers. These compounds were termed Dual Acting Virucidal Entry Inhibitors (DAVEI) compounds, and they induce specific, irreversible lysis of pseudotyped HIV-1 virions and fully infectious HIV-1 virions. Both components of the fusion, CVN and MPER, were found to be required, and that neither alone could induce virolysis, nor could they do so in a 1:1 mixture.

Example 2

Investigation of Mechanism of DAVEI MPER in Lytic Inactivation of HIV-1

While CVN binds to gp120 with high affinity and inhibits cell infection, it is non-lytic. MPER alone does not bind to the virus envelope with high affinity. Without wishing to be limited by any theory, the role of the CVN domain in DAVEI comprises binding to Env directly, while the MPER domain confers the lytic function once recruited to the virus. The mechanism of how the MPER domain engages the virus envelope in order to endow DAVEI with the HIV-1 lytic activity is herein investigated. In one aspect, mutagenesis is used to determine what components of DAVEI MPER are critical. In another aspect, virus membrane component modifications are used to assess the potential importance of membrane interactions with DAVEI MPER. In yet another aspect, direct binding analysis by Surface Plasmon Resonance (SPR) is used to examine the potential role of MPER-MPER interactions between DAVEI and Env. In yet another aspect, complementary virus Env mutations are used to determine possible roles of Env MPER and other membrane-interacting Env domains in the function of CVN-DAVEI.

Site Specific, Deleting and Truncating Mutations of the MPER Region in DAVEI:

The HIV-1 Env MPER region, when excised in peptides, has membrane-disruptive activities with potencies generally greater than 1 µM [24-26]. In contrast, in CVN-DAVEI, the MPER domain endows the chimera with sub-µM potency in both HIV-1 lysis and inactivation (FIGS. 2A, 4A and 6A). In certain embodiments, without wishing to be limited by any theory, three distinct features of MPER can promote engagement to virus envelope leading to the strong enhancement of the lytic and inactivation effect, which may be term the "DAVEI effect." In one aspect, the MPER sequence, 664-DKWASLWNWFEITEWLWYIK-683 (SEQ ID NO:21), contains 5 Trp residues within the overall predicted helical motif that facilitate binding of this region to membranes. In another aspect, the Cholesterol Recognition Amino Acid Consensus (CRAC) sequence at the C-terminus of MPER, 679-LWYIK-683 (SEQ ID NO:20) is >99% conserved across all HIV-1 clades, and binds to membrane cholesterol. In yet another aspect, MPER forms stable helical trimers in solution, and hence could potentially bind to the virus Env MPER, or to other epitopes on Env.

Using the recombinant CVN-DAVEI platform, residues predicted to be important for alternative modes of MPER-virus interaction are mutated, and their impacts on lysis are evaluated. In certain embodiments, mutations are cloned, starting with the CVN-DAVEI plasmid, mutated proteins are expressed in BL21 (DE3) PlysS cells and purified by Ni-NTA affinity chromatography using the His tag incorporated in the protein. Mutated proteins and unmodified CVN-DAVEI are compared for gp120 binding using Surface Plasmon Resonance (SPR) to ensure CVN function, and inhibition of human osteosarcoma (HOS) cell infection by HIV-1 BaL (produced from HEK-293T cells) to ensure antiviral activity. Derivatives exhibiting binding and antiviral functions are evaluated for ability to lyse HIV-1 using the p24 release ELISA assay.

For the W-rich region of MPER, W→A mutations exhibit stark drops in both infectivity and incorporation into virus particles, and also in reduced formation of the fusion pore. One-at-a-time or combinatorial W→A mutations in the MPER of CVN-DAVEI are performed to determine whether the W-rich surface of MPER helix plays a role in DAVEI-induced lysis.

Mutations of the CRAC domain shed light on cholesterol binding sensitivity to mutational variation. Conservative replacement of the Leu residue of LWYIK with other hydrophobic residues produces a spectrum of fusion abrogation correlated to decreased binding to cholesterol by 5-residue CRAC variants. Without wishing to be limited by any theory, if the lytic activity of CVN-DAVEI is dependent on cholesterol binding by the CRAC sequence, $EC_{50}$ for lysis varies as WT<L679A<L679V<L679I. Glycine mutants of the CRAC sequence, namely 679-GWGIK-683 and 679-LWGIG-683, also show strongly reduced ability to bind cholesterol. Gly mutations are thus examined for impact on CVN-DAVEI lysis. If individual residue changes do not show strong changes in lysis function, multiple mutations and truncation of the entire CRAC region are evaluated.

Cholesterol-Depleted Virus:

HIV envelope membrane contains up to 45 mol-% cholesterol, and interactions of the Env MPER CRAC sequence with membrane cholesterol are important for fusion. In certain embodiments, the MPER component of DAVEI also utilizes interactions with cholesterol for its activity. The extent of involvement of CRAC-cholesterol interactions in virolysis is investigated with viruses reversibly depleted of cholesterol by incubation with methyl-β-cyclodextrin (MβCD).

Figure 9:
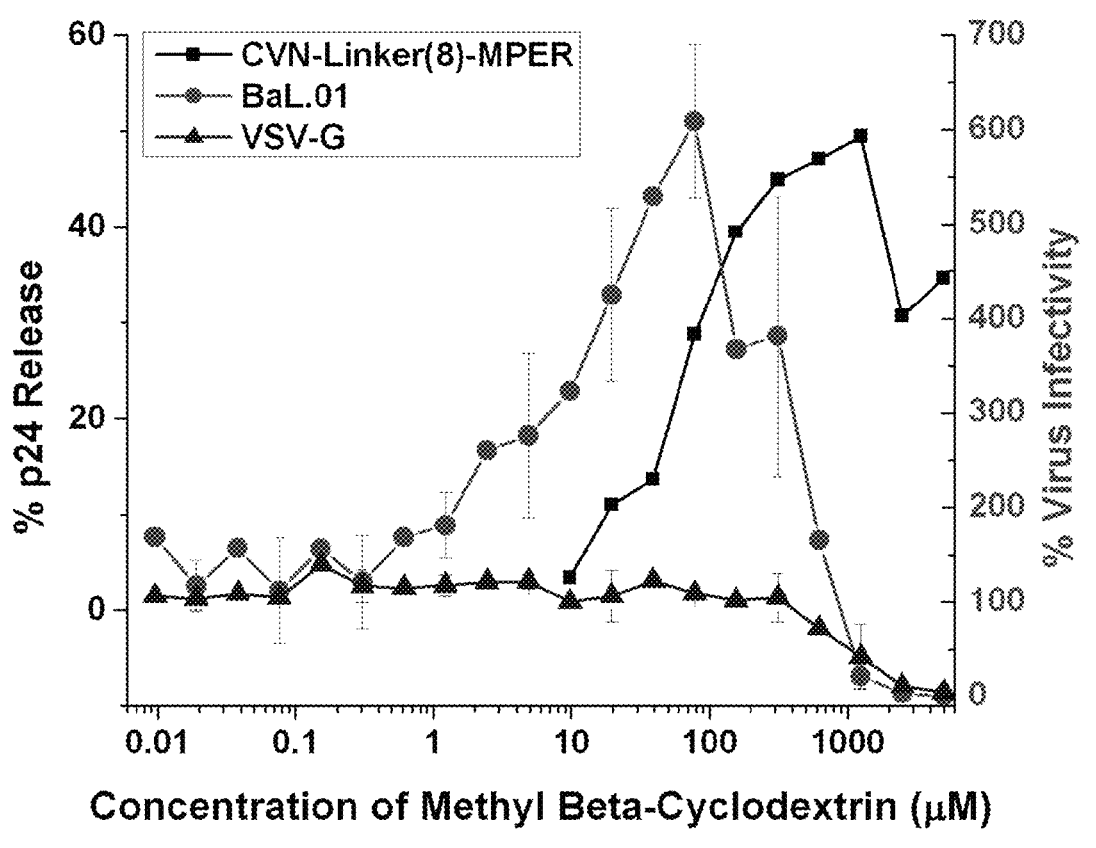

In a preliminary study (FIG. 9), moderate depletion of cholesterol by MβCD enhanced DAVEI virolysis, while further increasing [MβCD] ultimately led to suppression of lysis. A similar bimodal sensitivity though at different [MβCD] was observed in infectivity. These results suggest that membrane cholesterol plays a significant role in lysis, but does not distinguish what components of DAVEI or Env proteins are responsible for the effects.

Experiments of cholesterol depletion further include mutated CVN-DAVEI variants, focusing in particular on CRAC mutants and then mutations in the W-rich region. Using p24 sandwich ELISA, it is tested whether DAVEI mutants that have attenuated or minimal binding to cholesterol are sensitive to cholesterol depletion. Results with DAVEI MPER alanine mutants further inform on the importance of residues within MPER that cause lysis by interactions with cholesterol.

Direct DAVEI MPER Interactions with Exogenous MPER:

Free exogenous MPER was able to compete out CVN-DAVEI virolysis (FIG. 6A). The MPER sequence has a tendency to self-associate, and trimers of MPER have been observed. Thus, without wishing to be limited by any theory, DAVEI-MPER may cause lysis by specific MPER interactions with Env MPER, or by forming DAVEI multimers through the MPER domain, that are lytic through crosslinking the Env gp160 protomers in the virus spike or even through crosslinking of multiple spikes. DAVEI MPER interactions with various forms of exogenous MPER are investigated.

Using Surface Plasmon Resonance (SPR), it is determined whether DAVEI-MPER, including recombinant variants, binds to chip-immobilized MPER. The latter is synthesized with a terminal biotinyl group (Bt), and the consequent MPER-Bt is bound to streptavidin-functionalized sensor chips. DAVEI-MPER is flowed over the chip as soluble analyte. Negative controls include gp120, CVN or an irrelevant antibody. Binding of soluble MPER peptide itself as the analyte is also tested to resolve, not only if the MPER domain in DAVEI binds to MPER, but also if this interaction requires CVN fusion. Specificity of immobilized MPER interactions is assessed by using control flow cells containing other immobilized peptides, such as UM15 or larger peptide triazoles described elsewhere herein, that are not expected to bind MPER. Competition SPR is used to ensure that the MPER-MPER interactions detected are specific. For example, DAVEI-MPER interactions with immobilized MPER that occur through the analyte-immobilized ligand MPER regions should be competed by soluble MPER but not by CVN.

In addition, it is assessed whether or not the MPER domain in DAVEI binds spike MPER on virus. MPER binding to virus is measured using an ELISA assay, with pseudoviruses fixed using paraformaldehyde-glutaraldehyde and then adsorbed on ELISA plates. Binding of MPER-Bt to the pseudovirus Env protein is detected using a Strep-HRP conjugate. If binding is detected, specificity is tested by competition with increasing amounts of non-biotinylated MPER peptide as well as DAVEI. The sequence of Bt-MPER and virus Env MPER are modified to determine the residues responsible for DAVEI-MPER/virus-MPER interactions.

DAVEI Function of Mutations in Env MPER and Other Env Membrane Contact Regions:

It is tested whether the lytic functions of CVN-DAVEI and the variants thereof occur not only by direct effects of the virus MPER but also by indirect effects outside the MPER region. These investigations are carried out using mutated viruses modified in various regions of the envelope gp41, including not only MPER but also two other regions, the C-terminal intraviral tail (CT) and the transmembrane sequence (TM), that affect Env protein stability and MPER exposure.

The sequence of Env MPER is highly conserved and extremely sensitive to mutations. Hence, in certain embodiments, mutations to this region such as L679I within the CRAC sequence may destabilize potential interactions between Env MPER and DAVEI MPER. Mutations within the rest of MPER affect Env protein expression and incorporation within the virus, and are generated if the CRAC mutants are not successful. Site-directed mutagenesis is performed on the BaL.01 gp160 envelope plasmid and the mutated DNA is used to produce pseudoviruses expressing mutant MPER sequences. The pseudoviruses are tested with DAVEI compounds for lytic activity.

In certain embodiments, other Env protein mutations address the potential importance of Env structural elements in DAVEI function. In other embodiments, mutation R500T results in a cleavage deficiency in gp160; testing this mutation assesses the extent to which Env protein maturation is important for lysis. In yet other embodiments, the highly conserved mid-span Arg found in the transmembrane domain of gp41 may thin and possibly destabilize the envelope membrane in the vicinity of the spike protein. The R694A mutant may replace the polar R with an apolar residue allowing the membrane to become thicker and more stable. Without wishing to be limited by any theory, this makes the virus more resistant to DAVEI. In yet other embodiments, the C-terminal tail of gp41 is involved in intra-viral membrane interactions that have an impact on lytic inactivation. The gp41 cytoplasmic tail is truncated with a stop codon insertion at R704. Truncation affects HIV-1 function, including accelerating 6-helix bundle formation. In yet other embodiments, this may lead to enhanced lytic release with DAVEI.

In certain embodiments, Env mutants that accentuate the "DAVEI effect" of lytic inactivation by CVN-DAVEI, vs non-inactivating leakage only by MPER in isolated peptides provide tools to investigate the design of downstream DAVEI's.

In the event that some mutated forms of CVN-DAVEI do not express well, expression is pursued in alternate bacterial agents, such as BL21 (DE3) and Rosetta cells. In the vent that Env mutants express poorly, other virus isolates such as YU2 and JR-FLv are evaluated.

Example 3

Mechanism of Env Glycan Engagement and Stoichiometry of DAVEI:Env Spike Encounter Deconvoluting glycan engagement of DAVEI with the envelope spike protein helps define molecular arrangements that this class of compounds employs to inactivate HIV-1. The Env protein displays many Manα(1-2)Manα-terminated glycans, and CVN, with both low- and high-affinity glycan binding sites, has the capacity to bind to many of them. In contrast, the homologous lectin microvirin (MVN) has only a single glycan binding site and appears to bind to a smaller repertoire of such glycans. MVN exhibits antiviral activity against all HIV-1 group M clades with nanomolar $IC_{50}$ values (2-167 nM) (FIG. 10B). Moreover, MVN is less mitogenic than CVN and essentially non-toxic, making it an attractive clinical candidate. Hence, in certain embodiments, MVN-DAVEI is used to define glycan engagement and other aspects of engagement with Env that lead to DAVEI function.

Figure 10A:
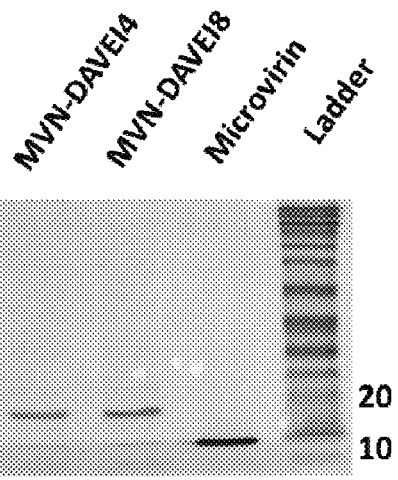
FIGS. 10A-10C illustrate MVN-based DAVEI.
Figure 10B:
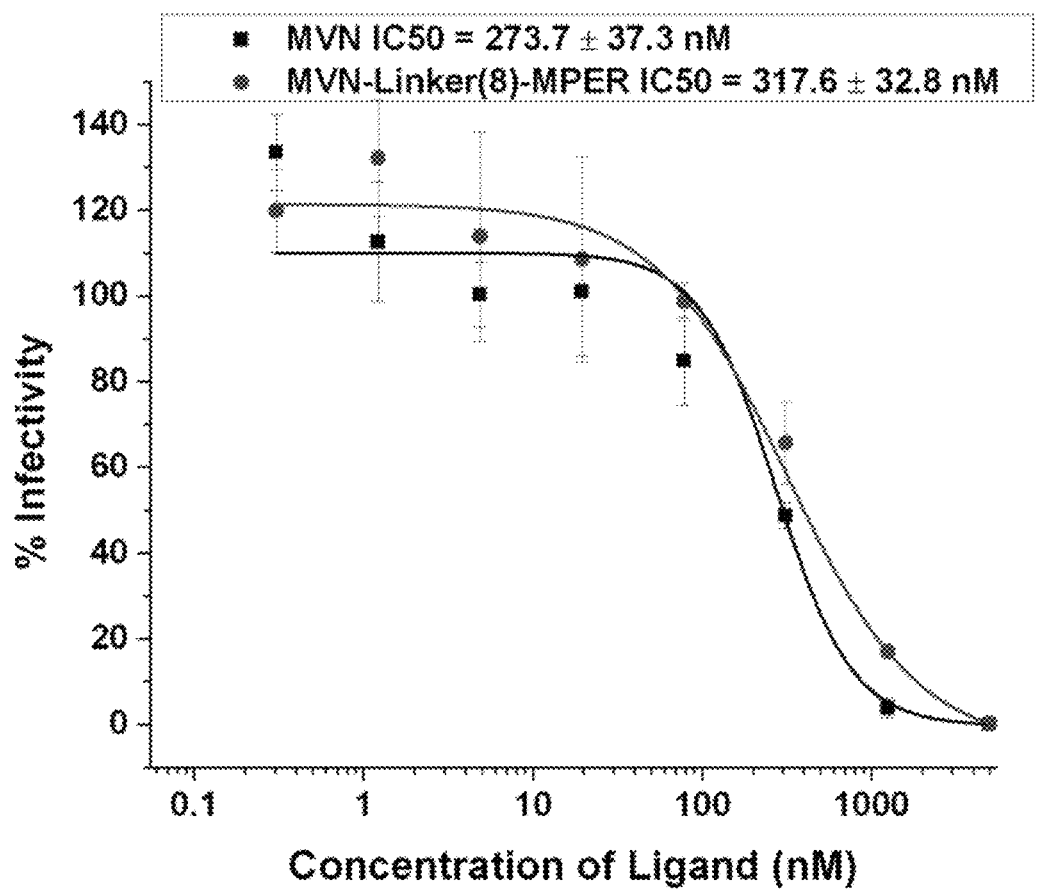
Figure 10C:
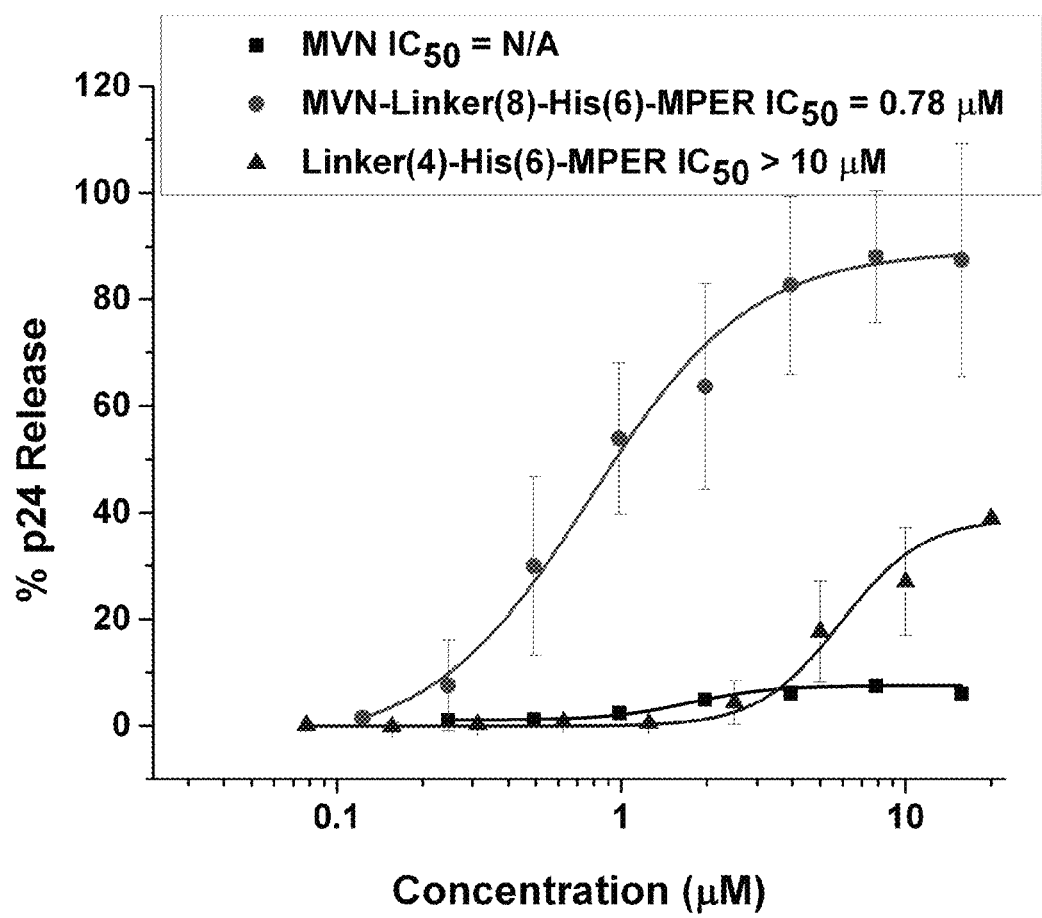

Preparation and Function of MVN-DAVEI:

MVN-based DAVEI's with antiviral and lytic activities are illustrated in FIGS. 10A-10C. MVN-DAVEI's were produced recombinantly using methods identical to those used for CVN-DAVEI. Briefly, MVN-linker-MPER fusion plasmids were transformed into BL21 (DE3) pLysS cells, and Kanamycin-resistant cells were induced with IPTG for protein production. Supernatant was loaded onto a Ni-NTA column and eluted using 250 mM imidazole solution. Eluted fractions were dialyzed on 1×PBS solution and loaded onto a size-exclusion column (Sephadex 20/60). Fractions containing protein were collected, analyzed via Coomassie stain on a 15% SDS PAGE gel (FIG. 10A). MVN-DAVEI displayed infectivity inhibition similar to that of MVN (FIG. 10B) and virolysis with an $EC_{50}$ of 0.78 µM (FIG. 10C). These data show that the lectin-based targeting role of DAVEI can be played by MVN as well as by CVN, with the resulting construct some 80-fold less potent. This indicates that MVN-DAVEI is useful as a tool for glycan mapping.

Figure 13B:
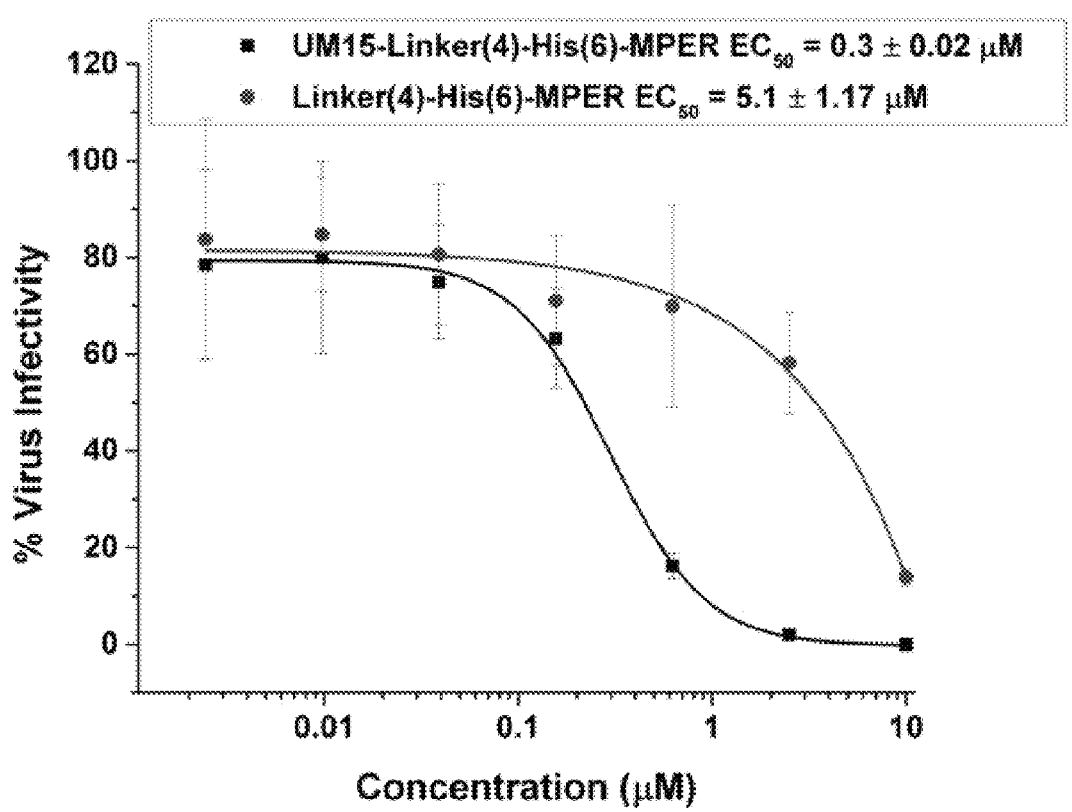

Mitigation of Non-Inactivating p24 Leakage by Linker-MPER in MVN-DAVEI:

Significant p24 leakage of the non-DAVEI, non-His-tagged $(G_4S)_4$-MPER ["linker(4)-MPER"] peptide was observed and this was not associated with equivalent virus inactivation (FIG. 13B). Here, differences between inactivating MVN-DAVEI lysis and non-inactivating linker-MPER leakage will be engineered using changes to the MPER sequence. For example, minimal MPER sequences as determined elsewhere herein, as well as those determined with linker-MPER, are incorporated. This effort allows to determine whether similar MPER domain mechanisms functioning with both CVN- and MVN-based DAVEI's generally. In certain embodiments, common features of MPER for both MVN- and CVN-DAVEI function may be used to construct simpler MPER domains. In other embodiments, this study helps identify an MVN-DAVEI construct with maximum lytic inactivation function and the incorporation of a linker-MPER with minimized non-inactivating leakage-only effect.

Env Glycan Dependence of MVN-DAVEI:

MVN-DAVEI opens up the opportunity to investigate which N-glycans on $gp120_{Bal}$ are required for the antiviral and virolytic properties of lectin-based DAVEI molecules. Correlating this glycan map with Env structure provides useful information on how to optimize linker lengths for other DAVEI's. Escape studies conducted with NL4.3 virus cultured in MT-4 cells in suboptimal dose of MVN identified four glycan specific MVN-resistance mutations after 41 passages. Of these, mutations at two sites, N295 and N392, were broadly resistant, while two others, N339 and N386, were less broadly resistant for multiple virus subtypes. Assuming that the fusion of MPER to MVN does not confer any alteration on the binding pattern of the MVN component to glycans on the envelope, studies presented herein identify which of these four residues are crucial for the lytic activity of MVN-DAVEI. Functional viruses are constructed, each containing a single mutation at one of these four sites. The viruses are tested for loss of MVN-DAVEI-induced lysis. If a single mutation in virus Env does not lead to loss of lytic function, a combination of double, triple or quadruple mutations is tested. In certain embodiments, certain specific subsets of these four glycan sites are responsible for lytic function.

Residues N339, N386 and N392 are important for CVN binding. Pseudoviruses with single, double or triple mutation at these glycan sites are tested with CVN-DAVEI. This helps deduce whether CVN- and MVN-DAVEI cause lytic inactivation via a similar set of glycans or, alternatively, whether CVN uses an alternative glycan footprint. If CVN-DAVEI remains lytically active (in other words, no resistance) with pseudoviruses containing mutations at the initial glycan positions N295, N339, N386 and N392, alternative glycan site positions related to CVN resistance are tested for resistance to CVN-DAVEI lytic inactivation.

Minimum Linker Length Between MVN and MPER Domains Using MVN-DAVEI:

CVN-DAVEI D4, with a linker containing 4 G4S repeats, had a potency similar to that of a CVN-DAVEI D8 with an 8-repeat linker length. In certain embodiments, length of the linker may be modified to alter potency. Since MVN-DAVEI has a single glycan binding site and may well bind with a simpler subset of Env gp120 glycans, a more clear-cut dependence of lysis on linker length is studied. MVN-DAVEI with a range of linker sizes are constructed, to determine the minimum size affording strong potency. A series of recombinant fusion proteins are produced having different numbers (0, 2, 4, 8, 16) of $(G_4S)$ linker repeat units between the MVN and MPER components. These proteins are expressed and purified analogously as described elsewhere herein.

Env Trimer Stoichiometry for MVN-DAVEI:

To assess the stoichiometry of protomers in the HIV-1 Env protein trimer that must be engaged by DAVE1 molecules that leads to inactivation, lysis with HIV-1 BaL.01 pseudotyped viruses containing different ratios of MVN-sensitive (WT, denoted W) and MVN-resistant (mutant, denoted M) forms of Env are analyzed. In the virus production protocol, typically 4 µg of gp160 DNA and 8 µg of plasmid that codes for virus core are used to transfect HEK293T cells. By changing the ratio of WT and M resistant gp160 DNA during virus production, virions with varying contents of W and M gp 160 on the virion surface are produced. The spike glycan site that cause loss of MVN-DAVEI lysis is/are used herein as the M variant. In certain embodiments, assuming that removal of MVN-sensitive glycans on a gp160 spike has no effect on spike gp160 incorporation, and further assuming a random protomer assortment within a virus spike, viruses containing trimers with different contents of W and M protomers, i.e., W3 (all wild type), M3 (all mutated), and hybrids (W2M and WM2) are obtained. The amount of each form of trimer depends on the amounts of DNA added for W and M (FIG. 11).

gp120 contents are ensured to be constant in viruses produced with different W and M compositions using ELISA. Total amounts of W and M gp120 are quantified by ELISA using D7324 antibody, which binds to the N-terminal region of gp120 and hence should bind equally to both the M and W forms. The relative content of gp120 are normalized against p24 content by immunoblot to equalize the virion amount used in assays. Once the virus properties are validated, they are tested for lytic activity with MVN-DAVEI. Here, the hypothesis that MVN-DAVEI lysis is strongly sensitive to reduced W3 (which will favor classes 1 and 2 for lytic activity) or whether mixtures containing substantial amounts of W2M and WM2 are also strongly lysed is assessed. If one W monomer per spike is sufficient to retain DAVEI sensitivity, substantial lysis for all variants except M3 is expected.

Models of MVN-DAVEI/Env Engagement to Define Possible MPER Interaction Sites on Env:

Glycosite mutations of C.2.3 are used to create initial docking poses for MVN-DAVEI on Env. The α(1,2)-mannobiose-bound NMR structure of MVN (PDB 2yhh; Shahzad-ul-Hussan, et al., 2011, J. Biol. Chem. 286(23):20788-20796) is used as a reference, and the MVN-bound mannobiose is aligned to glycosite mannobioses on the BG505-SOSIP.664 Env structure, and then MVN-DAVEI's are aligned to the MVN's. These models are subjected to enhanced sampling of the conformation of the linker-MPER segment using temperature-accelerated molecular dynamics. Samples from these simulations are used to propose MPER interaction sites on Env. SOSIP.664 displays α(1,2)-mannobioses only on the $Man_5$ glycan at N332. $Man_5$ glycans at asparagines are modelled-built at the MVN-sensitive positions 295, 339, 386, and 392 and equilibrated with all-atom MD. MVN-DAVEI8 are docked to glycans at any of these sites determined to be important elsewhere herein.

To illustrate this approach, a preliminary docking of 100 MVN-DAVEI8 conformations sampled from a 40-ns MD simulation to the BG505-SOSIP.664 structure with a model-built $Man_5$ glycan at N295 was conducted; a major pose for each α(1,2)-mannobiose was identified (FIG. 12). In certain embodiments, standard MD is insufficient to sample linker-MPER conformations that can reach the Env trimer when the MVN component is docked to the static SOSIP structure. This necessitates enhanced-sampling simulations of Env-DAVEI complex. In certain embodiments, this study identifies sites on the SOSIP.664 surface of the DAVEI MPER that can be reached given constraints of linker length and MVN binding site location.

Alternatively, CVN-DAVEI constructions are used, in which the low affinity site on CVN is mutationally removed to produce a simpler lectin DAVEI with which to investigate glycan engagement and related assembly properties. Two CVN variants that lack the low affinity glycan-binding site, but retain a fully functional high affinity site, have been derived by multiple mutations in the low affinity site. These mutants have identical $IC_{50}$ values as WT-CVN. Without wishing to be limited by any theory, monovalent interaction may be sufficient for antiviral activity. If DAVEI MPER's localize with high probability in the poorly resolved regions of the model, Env(–)ΔCT all-atom cryo model is used for similar docking studies. The Env(–)ΔCT has complete (but uncleaved) gp160 protomers up to and including the transmembrane domain, so that this Env construct can be modeled in a membrane, and it also has a near-complete set of glycans.

Example 4

Understanding Env Structure and Conformational Plasticity in the DAVEI Paradigm

These studies yield insights into the role of conformational transitions in Env that play a part in the virolysis mechanism. First, new DAVEI's using are produced existing gp120 targeting modules that avoid the glycan shield and that can modulate the gp120 conformational state to enable us to assess its impact on the DAVEI mechanism. A major question addressed is whether or not the "canonical" CD4-bound, or activated, conformation of gp120 in Env is accessed in the virolysis pathway. Second, the basis for non-inactivating leakage displayed by the linker-MPER constructs that do not contain a gp120-targeting module is addressed. Finally, further structural and mechanistic understanding in the form of all-atom models of complexes of Env with new small-molecule-based hunter-killer DAVEI's is gained. Combined, these activities help elucidate the role of Env conformational plasticity on the DAVEI mechanism.

Novel DAVEI's Generated from MPER Conjugated to Non-Lectin Gp120 Targeting Agents:

Using a peptide synthesis approach, linker-MPER sequences that permit a maximum DAVEI effect (i.e., linked lysis and infection inhibition), and at the same time express minimum non-productive virus lysis effects for the excised linker-MPER alone, are minimized. The synthetic results are correlated with recombinant analysis of MPER domains in CVN-DAVEI and in turn feed into MVN-DAVEI designs. Optimized DAVEI-effective linker-MPER sequences are be used in the design and synthesis of new generations of DAVE1 molecules.

Lectins do not conformationally activate Env, yet activated Env is among the forms of Env targeted by entry inhibitors. In certain embodiments, the invention provides smaller and more potent forms of DAVEI. In other embodiments, the invention provides DAVEI's comprising conjugates of peptide-based gp120-targeting agents with the MPER peptide. The length and the composition of the linker between the gp120-binder and MPER may be varied to fine tune activity. A non-limiting selection of gp120-targeting agents appears in Table 1.

TABLE 1

| gp120-targeting molecules. | | | | | |
|---|---|---|---|---|---|
| gp120 targeting module | Type | MW (Da) | conformationally activates Env? | causes gp120 shedding? | co-crystal structure with gp120? |
| CVN | lectin | 11,700 | No | No | No |
| MVN | lectin | 12,500 | No | No | No |
| UM15 | peptide triazole | 1005 | No | Yes | No |

Peptide triazoles (PT's) inhibit the interactions of HIV-1 gp120 with both CD4 and chemokine co-receptors. Virolytic activity of the novel MVN-based DAVEI's (FIG. 10C) supports the modularity of the DAVEI paradigm and indicates the gp120-binding role can be filled by agents other than CVN. However, CVN and MVN target glycans and, as a result, are likely sensitive to glycosite mutations. PT's are effective diverters of gp120 into non-activated conformations, permitting the exploration of the extent to which conformational control of gp120 is advantageous in the DAVEI mechanism. Because PT's are unique in this group, given their ability to commit Env to shed the resident gp120, PT-based DAVEI's are used to probe whether shedding is beneficial or detrimental to virolysis. gp120 Co-crystal structures provide a basis for molecular models of DAVEI/Env complexes to help identify possible MPER DAVEI interaction sites. In certain embodiments, truncated variants of MPER conjugated to small peptide gp120-targeting agents are hunter-killer molecules that can be readily produced for microbicide formulations of clinical significance.

Figure 13C:
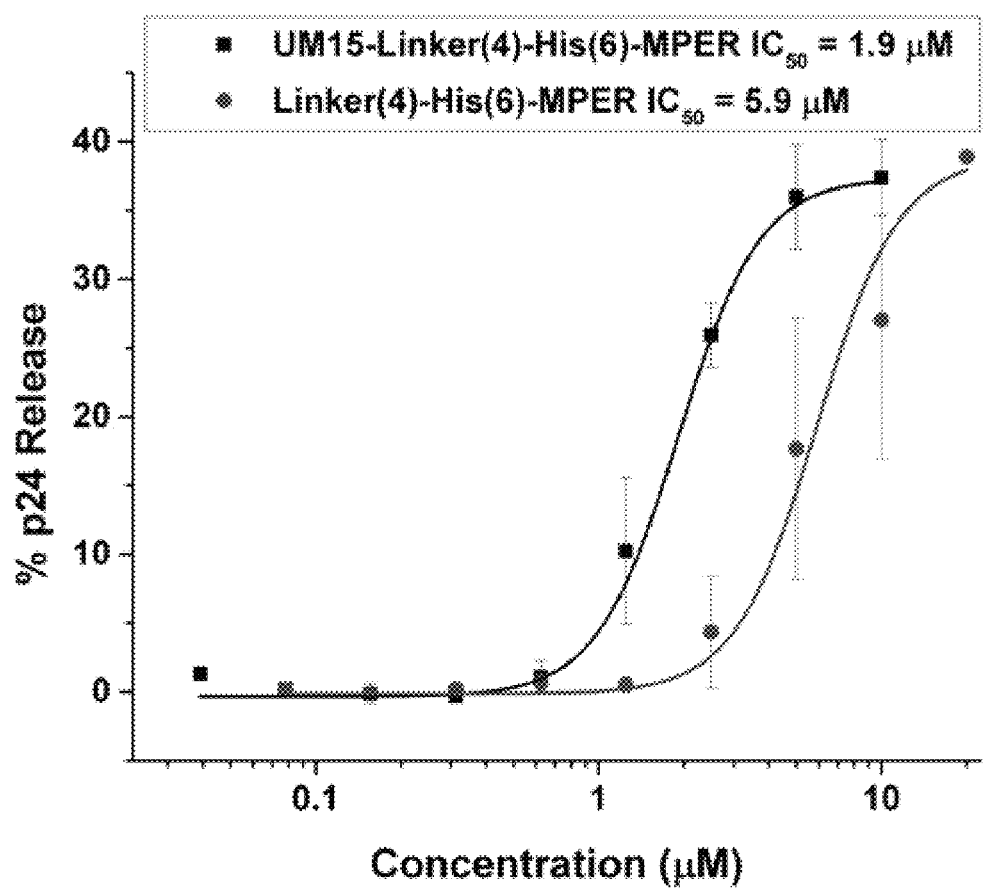

Peptide Triazole Conjugates:

The PT UM15 is a very active six-residue PT. UM15-DAVEI4 [UM15-$(G_4S)_4$-MPER] was synthesized (FIG. 13A) via Fmoc-based solid-phase peptide synthesis (SPPS), exploiting a CEM microwave system. The structure of the UM15-DAVEI4 conjugate was validated using matrix-assisted laser desorption ionization time-of-flight mass spectrometry (MALDI-TOF MS; measured mass 4964.56 Da; calculated 4964.20). UM15-DAVEI4 inhibited infection similar to UM15 alone (FIG. 13B), and a lytic activity some threefold greater than the $(G_4S)_4$-MPER ["linker(4)-MPER"] construct (FIG. 13C). These data demonstrate that UM15-DAVEI4 possesses promising virolytic activity, and more importantly, reveals for the first time DAVEI-class activity using a non-lectin-based targeting module. Further optimizations to this molecule include changing the linker length, optimizing the MPER component, and modifications to the UM15 component to use other PT's, including peptidomimetic variants.

Non-Inactivating p24 Leakage by Linker-MPER Constructs:

Shown alongside the data on UM15-DAVEI in FIGS. 13B-13C are data for the linker(4)-MPER constructs. Synthetic approaches are used to assess the impact of changing the MPER sequence on the non-inactivating p24 leakage of the linker-MPER constructs. All modified linker-MPER constructs showing significantly reduced non-inactivating leakage are incorporated into UM15 DAVEI's and small-molecule DAVEI's, to determine if reducing non-inactivating leakage of linker-MPER impacts DAVEI-effect lysis when a gp120-targeting agent is included. The impact of including the $H_6$ tag between the $(G_4S)$ linker and the MPER peptide (used in the recombinant DAVEI syntheses to aid purification) on non-inactivating leakage of the linker-MPER construct is assessed. In addition, additional experiments are performed on viruses lacking Env and viruses with non-HIV Envs (e.g., AMLV and VSV) to determine the extent of non-specificity of linker-MPER-induced leakage. Because UM15 induces gp120 shedding, 1:1 mixtures of UM15 and linker-MPER are examined. In certain embodiments, dose-response for lysis shifted to larger concentrations indicates that the UM15-MPER construct induces a genuine DAVEI effect.

Use of Models of Small-Molecule (SM)-Based DAVEI/Env Engagement to Probe Conformational Plasticity of Env:

State-of-the-art molecular modeling is used to determine linker lengths and Env conformations that are required, such that the MPER in the small-molecule/MPER conjugates reaches the virolytic active site. Molecular simulations and enhanced sampling are used to elucidate MPER interaction sites on trimeric Env structures in the context of PT-based DAVEI binding. Without wishing to be limited by any theory, such sites identified using the MVN-DAVEI models are also relevant for PT-DAVEI's, and as such modeling is used to determine linker lengths necessary for PT-DAVEI's. Docked models of PT's are used in the SOSIP.664 structure as the basis for models of MPER conjugates complexed with Env. Taken together, these studies provide an understanding, based on Env structures, of the optimal linker lengths for novel DAVEI conjugates.

The BG505 SOSIP.664 structure also serves as the launching point for large-scale conformational sampling simulations. The aim of these calculations is to access putative Env conformational states distinct from the activated state, against which docking of PT's compounds can be performed, and subsequently to build DAVEI-bound complexes that permit further evaluation of linker lengths. String-method calculations are used to characterize the thermodynamics of these transitions both with and without ligands. These studies provide an understanding at high resolution of the structural plasticity of Env and its role in virolysis.

Regarding the non-inactivating leakage induced by linker-MPER constructs, it may be that the BaL pseudovirus preparation yields a large fraction of "leaky" but infection-deficient virions that are the primary target of the linker-MPER constructs. Tests may be run for BaL mutants or other subtypes that exhibit a minimized leaky population of virus particles.

Alternatively, complexes using the atomically resolved Env(−)ΔCT precursor cryo structure are built and used to help establish MPER interaction sites and optimal linker lengths. The Env(−)ΔCT precursor structure is also used as a target for docking of PT to facilitate building these complex models.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound of formula (I), or a salt or solvate thereof:

BINDER-LINKER-SEQ ID NO:3 (I), wherein in (I) the BINDER binds to gp120, and the LINKER covalently connects the C-terminus of BINDER and the N-terminus of SEQ ID NO:3, wherein the BINDER comprises at least one selected from the group consisting of:

SEQ ID NO:1;

SEQ ID NO:12;

SEQ ID NO:22 ($X_1X_2X_3NIXWX_4$) (III), wherein in (III)

$X_1$ is absent or E, $X_2$ is selected from the group consisting of F,K,E,R, and Cit, $X_3$ is N or I, $X_4$ is S or T;

SEQ ID NO:23 (RINNIXW);

SEQ ID NO:24 (INNIXW);

SEQ ID NO:25 (NNIXWS);

SEQ ID NO:26 (INIXWS);

SEQ ID NO:27 (NNIXW);

wherein X is the modified proline of formula (IV)

wherein in (IV) R is selected from the group consisting of naphthyl,p-methyl phenyl, p-ethyl phenyl,2-phenylethyl and metallocene; and wherein the LINKER is a peptide of formula (II):

LINKER1-(LINKER2)$_n$ (II), wherein in (II) the LINKER1 comprises 1 to 60 amino acid residues; the LINKER2 comprises (His)$_6$ (SEQ ID NO:5) or AspTyrLysAspAspAspAspLys (SEQ ID NO:9), and 'n' is 0 or 1.

2. The compound of claim 1, wherein the metallocene is ferrocene.

3. The compound of claim 1, wherein the LINKER1 comprises 10 to 50 neutral amino acid residues selected from the group consisting of glycine and serine residues.

4. The compound of claim 1, wherein the LINKER1 comprises 2 to 10 repeating units of a pentapeptide consisting of neutral amino acid residues.

5. The compound of claim 4, wherein the neutral amino acid residues are selected from the group consisting of glycine and serine residues.

6. The compound of claim 4, wherein the LINKER1 comprises (SEQ ID NO:6)$_m$ or (SEQ ID NO:10)-(SEQ ID NO:6)$_m$, wherein 'm' is an integer ranging from 2 to 10.

7. The compound of claim 6, wherein the LINKER1 comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$ or Ser-(SEQ ID NO:6)$_2$-Gly-(SEQ ID NO:6)-Gly-(SEQ ID NO:6)$_5$.

8. The compound of claim 1, wherein the LINKER comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$, Ser-(SEQ ID NO:6)$_2$-Gly-(SEQ ID NO:6)-Gly-(SEQ ID NO:6)$_5$, (SEQ ID NO:6)$_4$-(SEQ ID NO:5), (SEQ ID NO:10)-(SEQ ID NO:6)$_4$-(SEQ ID NO:5), (SEQ ID NO:6)$_8$-(SEQ ID NO:5), (SEQ ID NO:10)-(SEQ ID NO:6)$_8$-(SEQ ID NO:5), Ser-(SEQ ID NO:6)$_2$-Gly-(SEQ ID NO:6)-Gly-(SEQ ID NO:6)$_5$-(SEQ ID NO:5), (SEQ ID NO:6)$_4$-(SEQ ID NO:9), (SEQ ID NO:10)-(SEQ ID NO:6)$_4$-(SEQ ID NO:9), (SEQ ID NO:6)$_8$-(SEQ ID NO:9), (SEQ ID NO:10)-(SEQ ID NO:6)$_8$-(SEQ ID NO:9), or Ser-(SEQ ID NO:6)$_2$-Gly-(SEQ ID NO:6)-Gly-(SEQ ID NO:6)$_5$-(SEQ ID NO:9).

9. The compound of claim 1, wherein the compound of formula (I) comprises at least one selected from the group consisting of

SEQ ID NO:1-(SEQ ID NO:10)$_{0-1}$-(SEQ ID NO:6)$_4$-SEQ ID NO:5-SEQ ID NO:3;

SEQ ID NO:1-(SEQ ID NO:10)$_{0-1}$-(SEQ ID NO:6)$_4$-SEQ ID NO:3;

SEQ ID NO:1-(SEQ ID NO:10)$_{0-1}$-(SEQ ID NO:6)$_8$-SEQ ID NO:5-SEQ ID NO:3;

SEQ ID NO:1-(SEQ ID NO:10)$_{0-1}$-(SEQ ID NO:6)$_8$-SEQ ID NO:3;

SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:1-Ser-(SEQ ID NO:6)$_2$-Gly-(SEQ ID NO:6)-Gly-(SEQ ID NO:6)$_5$-SEQ ID NO:3;
SEQ ID NO:12-(SEQ ID NO:10)$_{0-1}$-(SEQ ID NO:6)$_4$-SEQ ID NO:5-SEQ ID NO:3;
SEQ ID NO:12-(SEQ ID NO:10)$_{0-1}$-(SEQ ID NO:6)$_4$-SEQ ID NO:3;
SEQ ID NO:12-(SEQ ID NO:10)$_{0-1}$-(SEQ ID NO:6)$_8$-SEQ ID NO:5-SEQ ID NO:3;
SEQ ID NO:12-(SEQ ID NO:10)$_{0-1}$-(SEQ ID NO:6)$_8$-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:3;
and combinations thereof.

10. A pharmaceutical composition comprising the compound of claim 1 and at least one pharmaceutically acceptable carrier.

11. The composition of claim 10, further comprising at least one additional agent useful for treating HIV infections.

12. The composition of claim 11, wherein the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof.

13. A method of promoting HIV-1 virolysis, the method comprising contacting HIV-1 with an effective amount of at least one compound of claim 1, whereby HIV-1 undergoes virolysis.

14. The method of claim 13, wherein the LINKER1 comprises 2 to 10 repeating units of a pentapeptide consisting of neutral amino acid residues selected from the group consisting of glycine and serine residues.

15. The method of claim 14, wherein the LINKER1 comprises (SEQ ID NO:6)$_m$ or (SEQ ID NO:10)-(SEQ ID NO:6)$_m$, wherein 'm' is an integer ranging from 2 to 10.

16. The method of claim 13, wherein the LINKER comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$, Ser-(SEQ ID NO:6)$_2$-Gly-(SEQ ID NO:6)-Gly-(SEQ ID NO:6)$_5$, (SEQ ID NO:6)$_4$-(SEQ ID NO:5), (SEQ ID NO:10)-(SEQ ID NO:6)$_4$-(SEQ ID NO:5), (SEQ ID NO:6)$_8$-(SEQ ID NO:5), (SEQ ID NO:10)-(SEQ ID NO:6)$_8$-(SEQ ID NO:5), Ser-(SEQ ID NO:6)$_2$-Gly-(SEQ ID NO:6)-Gly-(SEQ ID NO:6)$_5$-(SEQ ID NO:5), (SEQ ID NO:6)$_4$-(SEQ ID NO:9), (SEQ ID NO:10)-(SEQ ID NO:6)$_4$-(SEQ ID NO:9), (SEQ ID NO:6)$_8$-(SEQ ID NO:9), (SEQ ID NO:10) (SEQ ID NO:6)$_8$-(SEQ ID NO:9), or Ser-(SEQ ID NO:6)$_2$-Gly-(SEQ ID NO:6)-Gly-(SEQ ID NO:6)$_5$-(SEQ ID NO:9).

17. The method of claim 13, wherein the compound of formula (I) comprises at least one selected from the group consisting of:
SEQ ID NO:1-(SEQ ID NO:10)$_{0-1}$-(SEQ ID NO:6)$_4$-SEQ ID NO:5-SEQ ID NO:3;
SEQ ID NO:1-(SEQ ID NO:10)$_{0-1}$-(SEQ ID NO:6)$_4$-SEQ ID NO:3;
SEQ ID NO:1-(SEQ ID NO:10)$_{0-1}$-(SEQ ID NO:6)$_8$-SEQ ID NO:5-SEQ ID NO:3;
SEQ ID NO:1-(SEQ ID NO:10)$_{0-1}$-(SEQ ID NO:6)$_8$-SEQ ID NO:3;
SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:1-Ser-(SEQ ID NO:6)$_2$-Gly-(SEQ ID NO:6)-Gly-(SEQ ID NO:6)$_5$-SEQ ID NO:3;
SEQ ID NO:12-(SEQ ID NO:10)$_{0-1}$-(SEQ ID NO:6)$_4$-SEQ ID NO:5-SEQ ID NO:3;
SEQ ID NO:12-(SEQ ID NO:10)$_{0-1}$-(SEQ ID NO:6)$_4$-SEQ ID NO:3;
SEQ ID NO:12-(SEQ ID NO:10)$_{0-1}$-(SEQ ID NO:6)$_8$-SEQ ID NO:5-SEQ ID NO:3;
SEQ ID NO:12-(SEQ ID NO:10)$_{0-1}$-(SEQ ID NO:6)$_8$-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:3;
and combinations thereof.

18. The method of claim 13, wherein the HIV-1 is present in the body of a mammal.

19. The method of claim 18, wherein the mammal is human.

20. A method of treating HIV-1 infection in a mammal in need thereof, the method comprising administering to the mammal a therapeutically effective amount of at least one compound of claim 1, whereby administration of the compound treats HIV-1 infection.

21. The method of claim 20, wherein the LINKER1 comprises (SEQ ID NO:6)$_m$ or (SEQ ID NO:10)-(SEQ ID NO:6)$_m$, wherein 'm' is an integer ranging from 2 to 10.

22. The method of claim 20, wherein the LINKER comprises (SEQ ID NO:6)$_4$, (SEQ ID NO:10)-(SEQ ID NO:6)$_4$, (SEQ ID NO:6)$_8$, (SEQ ID NO:10)-(SEQ ID NO:6)$_8$, Ser-(SEQ ID NO:6)$_2$-Gly-(SEQ ID NO:6)-Gly-(SEQ ID NO:6)$_5$, (SEQ ID NO:6)$_4$-(SEQ ID NO:5), (SEQ ID NO:10)-(SEQ ID NO:6)$_4$-(SEQ ID NO:5), (SEQ ID NO:6)$_8$-(SEQ ID NO:5), (SEQ ID NO:10)-(SEQ ID NO:6)$_8$-(SEQ ID NO:5), Ser-(SEQ ID NO:6)$_2$-Gly-(SEQ ID NO:6)-Gly-(SEQ ID NO:6)$_5$ (SEQ ID NO:5), (SEQ ID NO:6)$_4$-(SEQ ID NO:9), (SEQ ID NO:10)-(SEQ ID NO:6)$_4$-(SEQ ID NO:9), (SEQ ID NO:6)$_8$-(SEQ ID NO:9), (SEQ ID NO:10)-(SEQ ID NO:6)$_8$-(SEQ ID NO:9), or Ser-(SEQ ID NO:6)$_2$-Gly-(SEQ ID NO:6)-Gly-(SEQ ID NO:6)$_5$-(SEQ ID NO:9).

23. The method of claim 20, wherein the compound of formula (I) comprises at least one selected from the group consisting of:
SEQ ID NO:1-(SEQ ID NO:10)$_{0-1}$-(SEQ ID NO:6)$_4$-SEQ ID NO:5-SEQ ID NO:3;
SEQ ID NO:1-(SEQ ID NO:10)$_{0-1}$-(SEQ ID NO:6)$_4$-SEQ ID NO:3;
SEQ ID NO:1-(SEQ ID NO:10)$_{0-1}$-(SEQ ID NO:6)$_8$-SEQ ID NO:5-SEQ ID NO:3;
SEQ ID NO:1-(SEQ ID NO:10)$_{0-1}$-(SEQ ID NO:6)$_8$-SEQ ID NO:3;
SEQ ID NO:1-Ser-(SEQ ID NO:6)$_2$-Gly-(SEQ ID NO:6)-Gly-(SEQ ID NO:6)$_5$-SEQ ID NO:5-SEQ ID NO:3;
SEQ ID NO:1-Ser-(SEQ ID NO:6)$_2$-Gly-(SEQ ID NO:6)-Gly-(SEQ ID NO:6)$_5$-SEQ ID NO:3;
SEQ ID NO:12-(SEQ ID NO:10)$_{0-1}$-(SEQ ID NO:6)$_4$-SEQ ID NO:5-SEQ ID NO:3;
SEQ ID NO:12-(SEQ ID NO:10)$_{0-1}$-(SEQ ID NO:6)$_4$-SEQ ID NO:3;
SEQ ID NO:12-(SEQ ID NO:10)$_{0-1}$-(SEQ ID NO:6)$_8$-SEQ ID NO:5-SEQ ID NO:3;
SEQ ID NO:12-(SEQ ID NO:10)$_{0-1}$-(SEQ ID NO:6)$_8$-SEQ ID NO:3;
SEQ ID NO:12-Ser-(SEQ ID NO:6)$_2$-Gly-(SEQ ID NO:6)-Gly-(SEQ ID NO:6)$_5$-SEQ ID NO:5-SEQ ID NO:3;

SEQ ID NO:12-Ser-(SEQ ID NO:6)$_2$-Gly-(SEQ ID NO:6)-Gly-(SEQ ID NO:6)$_5$-SEQ ID NO:3;

and combinations thereof.

24. The method of claim 20, wherein the mammal is further administered at least one additional agent useful for treating HIV infections, wherein the at least one additional agent is selected from the group consisting of HIV combination drugs, entry and fusion inhibitors, integrase inhibitors, non-nucleoside reverse transcriptase inhibitors, nucleoside reverse transcriptase inhibitors, protease inhibitors, and combinations thereof.

25. The method of claim 24, wherein the at least one additional agent and the compound are co-formulated.

26. The method of claim 20, wherein the composition is administered to the mammal orally, nasally, rectally, intravaginally, parenterally, buccally, sublingually, intragastrically or topically.

27. The method of claim 20, wherein the mammal is human.

* * * * *

SEQUENCE LISTING

<160> NUMBER OF SEQ ID NOS: 36

<210> SEQ ID NO 1
<211> LENGTH: 101
<212> TYPE: PRT
<213> ORGANISM: Artificial Sequence
<220> FEATURE:
<223> OTHER INFORMATION: chemically synthesized; cyanovirin-N fragment

<400> SEQUENCE: 1

Leu Gly Lys Phe Ser Gln Thr Cys Tyr Asn Ser Ala Ile Gln Gly Ser
1               5                   10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
             85                  90                  95

Thr Leu Lys Tyr Glu
            100

<210> SEQ ID NO 2
<211> LENGTH: 303
<212> TYPE: DNA
<213> ORGANISM: Artificial Sequence
<220> FEATURE:
<223> OTHER INFORMATION: chemically synthesized; cyanovirin-N fragment

<400> SEQUENCE: 2
cttggtaaat tctcccagac ctgctacaac tccgctatcc agggttccgt tctgacctcc      60
acctgcgaac gtaccaacgg tggttacaac acctcctcca tcgacctgaa ctccgttatc     120
gaaaacgttg acggttccct gaatggcag ccgtccaact tcatcgaaac ctgccgtaac      180
acccagctgg ctggttcctc cgaactggct gctgaatgca aaccccgtgc tcagcagttc     240
gtttccacca aatcaacct ggacgaccac atcgctaaca tcgacggtac cctgaaatac     300
gaa                                                                   303

<210> SEQ ID NO 3
<211> LENGTH: 25
<212> TYPE: PRT
<213> ORGANISM: Artificial Sequence
<220> FEATURE:
<223> OTHER INFORMATION: chemically synthesized; MPER fragment
<220> FEATURE:
<221> NAME/KEY: MISC_FEATURE
<222> LOCATION: (1)..(1)
<223> OTHER INFORMATION: Asp, Glu, Asn or absent
<220> FEATURE:
<221> NAME/KEY: MISC_FEATURE
<222> LOCATION: (2)..(2)
<223> OTHER INFORMATION: Leu or absent
<220> FEATURE:
<221> NAME/KEY: MISC_FEATURE
<222> LOCATION: (3)..(3)
<223> OTHER INFORMATION: Leu or absent
<220> FEATURE:
<221> NAME/KEY: MISC_FEATURE
<222> LOCATION: (4)..(4)
<223> OTHER INFORMATION: Ala, Glu, Lys, Gln, Asp, Ser, Thr or absent
<220> FEATURE:
<221> NAME/KEY: MISC_FEATURE
<222> LOCATION: (5)..(5)
<223> OTHER INFORMATION: Leu or absent
<220> FEATURE:
<221> NAME/KEY: MISC_FEATURE
<222> LOCATION: (7)..(7)
<223> OTHER INFORMATION: Lys, Ser, Gln, Thr or Asn
<220> FEATURE:
<221> NAME/KEY: MISC_FEATURE
<222> LOCATION: (9)..(9)
<223> OTHER INFORMATION: Ala, Asp, Lys, Asn, Gln or Thr
<220> FEATURE:
<221> NAME/KEY: MISC_FEATURE
<222> LOCATION: (10)..(10)
<223> OTHER INFORMATION: Ser, Asn, Thr or Asp
<220> FEATURE:
<221> NAME/KEY: MISC_FEATURE
<222> LOCATION: (13)..(13)
<223> OTHER INFORMATION: Asn, Ser or Thr
<220> FEATURE:
<221> NAME/KEY: MISC_FEATURE
<222> LOCATION: (16)..(16)
<223> OTHER INFORMATION: Glu, Asp, Ser, Asn, Thr or Gly
<220> FEATURE:
<221> NAME/KEY: MISC_FEATURE
<222> LOCATION: (18)..(18)
<223> OTHER INFORMATION: Thr or Ser

```
<220> FEATURE:
<221> NAME/KEY: MISC_FEATURE
<222> LOCATION: (19)..(19)
<223> OTHER INFORMATION: Glu, Asn, Lys, Gln, Arg or His
<220> FEATURE:
<221> NAME/KEY: MISC_FEATURE
<222> LOCATION: (25)..(25)
<223> OTHER INFORMATION: Lys, Arg or Glu

<400> SEQUENCE: 3

Xaa Xaa Xaa Xaa Xaa Asp Xaa Trp Xaa Xaa Leu Trp Xaa Trp Phe Xaa
1               5                   10                  15

Ile Xaa Xaa Trp Leu Trp Tyr Ile Xaa
            20                  25

<210> SEQ ID NO 4
<211> LENGTH: 60
<212> TYPE: DNA
<213> ORGANISM: Artificial Sequence
<220> FEATURE:
<223> OTHER INFORMATION: chemically synthesized; MPER fragment

<400> SEQUENCE: 4
gacaaatggg caagtttgtg gaattggttt gaaataacag aatggctgtg gtatataaaa    60

<210> SEQ ID NO 5
<211> LENGTH: 6
<212> TYPE: PRT
<213> ORGANISM: Artificial Sequence
<220> FEATURE:
<223> OTHER INFORMATION: chemically synthesized

<400> SEQUENCE: 5

His His His His His His
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized

<400> SEQUENCE: 6

Gly Gly Gly Gly Ser
1               5

<210> SEQ ID NO 7
<211> LENGTH: 43
<212> TYPE: DNA
<213> ORGANISM: Artificial Sequence
<220> FEATURE:
<223> OTHER INFORMATION: chemically synthesized

<400> SEQUENCE: 7
ttttggatcc catcatcatc atcatcatga caaatgggca agt                      43

<210> SEQ ID NO 8
<211> LENGTH: 31
<212> TYPE: DNA
<213> ORGANISM: Artificial Sequence
<220> FEATURE:
<223> OTHER INFORMATION: chemically synthesized

<400> SEQUENCE: 8
ataatgaata gagttaggta aaagtccggg t                                   31
```

<210> SEQ ID NO 9
<211> LENGTH: 8
<212> TYPE: PRT
<213> ORGANISM: Artificial Sequence
<220> FEATURE:
<223> OTHER INFORMATION: chemically synthesized; flag epitope tag

<400> SEQUENCE: 9

```
Asp Tyr Lys Asp Asp Asp Asp Lys
1               5
```

<210> SEQ ID NO 10
<211> LENGTH: 2
<212> TYPE: PRT
<213> ORGANISM: Artificial Sequence
<220> FEATURE:
<223> OTHER INFORMATION: chemically synthesized

<400> SEQUENCE: 10

```
Gly Ser
1
```

<210> SEQ ID NO 11
<211> LENGTH: 23
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Leu or absent
<220> FEATURE:
<221> NAME/KEY: MISC_FEATURE
<222> LOCATION: (2)..(2)
<223> OTHER INFORMATION: Leu or absent
<220> FEATURE:
<221> NAME/KEY: MISC_FEATURE
<222> LOCATION: (3)..(3)
<223> OTHER INFORMATION: Leu or absent

<400> SEQUENCE: 11

```
Xaa Xaa Xaa Asp Lys Trp Ala Ser Leu Trp Asn Trp Phe Glu Ile Thr
1               5                   10                  15

Glu Trp Leu Trp Tyr Ile Lys
            20
```

<210> SEQ ID NO 12
<211> LENGTH: 108
<212> TYPE: PRT
<213> ORGANISM: Artificial Sequence
<220> FEATURE:
<223> OTHER INFORMATION: chemically synthesized; microvirin

<400> SEQUENCE: 12

```
Met Pro Asn Phe Ser His Thr Cys Ser Ser Ile Asn Tyr Asp Pro Asp
1               5                   10                  15

Ser Thr Ile Leu Ser Ala Glu Cys Gln Ala Arg Asp Gly Glu Trp Leu
            20                  25                  30

Pro Thr Glu Leu Arg Leu Ser Asp His Ile Gly Asn Ile Asp Gly Glu
        35                  40                  45

Leu Gln Phe Gly Asp Gln Asn Phe Gln Glu Thr Cys Gln Asp Cys Arg
    50                  55                  60

Leu Glu Phe Gly Asp Gly Glu Gln Ser Val Trp Leu Val Cys Thr Cys
65                  70                  75                  80
```

Gln Thr Met Asp Gly Glu Trp Lys Ser Thr Gln Ile Leu Leu Asp Ser
            85                  90                  95

Gln Ile Asp Asn Asn Asp Ser Gln Leu Glu Ile Gly
            100                 105

<210> SEQ ID NO 13
<211> LENGTH: 31
<212> TYPE: DNA
<213> ORGANISM: Artificial Sequence
<220> FEATURE:
<223> OTHER INFORMATION: chemically synthesized

<400> SEQUENCE: 13
ggtggaggcg ggtcccatca tcatcatcat c                                    31

<210> SEQ ID NO 14
<211> LENGTH: 31
<212> TYPE: DNA
<213> ORGANISM: Artificial Sequence
<220> FEATURE:
<223> OTHER INFORMATION: chemically synthesized

<400> SEQUENCE: 14
gaaggagata tacacatgaa atacctgctg c                                    31

<210> SEQ ID NO 15
<211> LENGTH: 31
<212> TYPE: DNA
<213> ORGANISM: Artificial Sequence
<220> FEATURE:
<223> OTHER INFORMATION: chemically synthesized

<400> SEQUENCE: 15
ccagccggcg atgcatatgg gtaaattctc c                                    31

<210> SEQ ID NO 16
<211> LENGTH: 35
<212> TYPE: DNA
<213> ORGANISM: Artificial Sequence
<220> FEATURE:
<223> OTHER INFORMATION: chemically synthesized

<400> SEQUENCE: 16
ggtaccctga aatacgaagg atccggtggc ggagg                                35

<210> SEQ ID NO 17
<211> LENGTH: 34
<212> TYPE: DNA
<213> ORGANISM: Artificial Sequence
<220> FEATURE:
<223> OTHER INFORMATION: chemically synthesized

<400> SEQUENCE: 17
ccaactggaa attggatccg atccggctgc taac                                 34

<210> SEQ ID NO 18
<211> LENGTH: 34
<212> TYPE: DNA
<213> ORGANISM: Artificial Sequence
<220> FEATURE:
<223> OTHER INFORMATION: chemically synthesized

<400> SEQUENCE: 18
ggtgccgcgc ggccatatgc ctaattttc gcac                                  34

-continued

```
<210> SEQ ID NO 19
<211> LENGTH: 18
<212> TYPE: DNA
<213> ORGANISM: Artificial Sequence
<220> FEATURE:
<223> OTHER INFORMATION: chemically synthesized; His6 tag

<400> SEQUENCE: 19
catcatcatc atcatcat                                                 18

<210> SEQ ID NO 20
<211> LENGTH: 5
<212> TYPE: PRT
<213> ORGANISM: Artificial Sequence
<220> FEATURE:
<223> OTHER INFORMATION: chemically synthesized

<400> SEQUENCE: 20

Leu Trp Tyr Ile Lys
1               5

<210> SEQ ID NO 21
<211> LENGTH: 20
<212> TYPE: PRT
<213> ORGANISM: Artificial Sequence
<220> FEATURE:
<223> OTHER INFORMATION: chemically synthesized

<400> SEQUENCE: 21

Asp Lys Trp Ala Ser Leu Trp Asn Trp Phe Glu Ile Thr Glu Trp Leu
1               5                   10                  15

Trp Tyr Ile Lys
            20

<210> SEQ ID NO 22
<211> LENGTH: 8
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Glu or absent
<220> FEATURE:
<221> NAME/KEY: MISC_FEATURE
<222> LOCATION: (2)..(2)
<223> OTHER INFORMATION: Phe, Lys, Glu, Arg, or Cittruline
<220> FEATURE:
<221> NAME/KEY: MISC_FEATURE
<222> LOCATION: (3)..(3)
<223> OTHER INFORMATION: Asn or Ile
<220> FEATURE:
<221> NAME/KEY: MISC_FEATURE
<222> LOCATION: (6)..(6)
<223> OTHER INFORMATION: modified proline of formula (IV)
<220> FEATURE:
<221> NAME/KEY: MISC_FEATURE
<222> LOCATION: (8)..(8)
<223> OTHER INFORMATION: Ser or Thr

<400> SEQUENCE: 22

Xaa Xaa Xaa Asn Ile Xaa Trp Xaa
1               5

<210> SEQ ID NO 23
<211> LENGTH: 7
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: modified proline of formula (IV)

<400> SEQUENCE: 23

Arg Ile Asn Asn Ile Xaa Trp
1               5

<210> SEQ ID NO 24
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (5)..(5)
<223> OTHER INFORMATION: modified proline of formula (IV)

<400> SEQUENCE: 24

Ile Asn Asn Ile Xaa Trp
1               5

<210> SEQ ID NO 25
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (4)..(4)
<223> OTHER INFORMATION: modified proline of formula (IV)

<400> SEQUENCE: 25

Asn Asn Ile Xaa Trp Ser
1               5

<210> SEQ ID NO 26
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (4)..(4)
<223> OTHER INFORMATION: modified proline of formula (IV)

<400> SEQUENCE: 26

Ile Asn Ile Xaa Trp Ser
1               5

<210> SEQ ID NO 27
<211> LENGTH: 5
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (4)..(4)
<223> OTHER INFORMATION: modified proline of formula (IV)

<400> SEQUENCE: 27

Asn Asn Ile Xaa Trp
1               5
```

```
<210> SEQ ID NO 28
<211> LENGTH: 22
<212> TYPE: PRT
<213> ORGANISM: Artificial Sequence
<220> FEATURE:
<223> OTHER INFORMATION: chemically synthesized; pelB
<220> FEATURE:
<221> NAME/KEY: MISC_FEATURE
<222> LOCATION: (22)..(22)
<223> OTHER INFORMATION: Ala or His

<400> SEQUENCE: 28

Met Lys Tyr Leu Leu Pro Thr Ala Ala Ala Gly Leu Leu Leu Leu Ala
1               5                   10                  15

Thr Gln Pro Ala Met Xaa
            20

<210> SEQ ID NO 29
<211> LENGTH: 66
<212> TYPE: DNA
<213> ORGANISM: Artificial Sequence
<220> FEATURE:
<223> OTHER INFORMATION: chemically synthesized; pelB

<400> SEQUENCE: 29
atgaaatacc tgctgccgac cgctgctgct ggtctgctgc tcctcgctac ccagccggcg      60
atggcc                                                                66

<210> SEQ ID NO 30
<211> LENGTH: 33
<212> TYPE: DNA
<213> ORGANISM: Artificial Sequence
<220> FEATURE:
<223> OTHER INFORMATION: chemically synthesized; NFV(ochre)L(ochre)EGDIH

<400> SEQUENCE: 30
aattttgttt aactttaaga aggagatata cat                                   33

<210> SEQ ID NO 31
<211> LENGTH: 54
<212> TYPE: DNA
<213> ORGANISM: Artificial Sequence
<220> FEATURE:
<223> OTHER INFORMATION: chemically synthesized;
      (ochre)(ochre)(ochre)KLAAALEHHHHHH(opal)D

<400> SEQUENCE: 31
taataataaa agcttgcggc cgcactcgag caccaccacc accaccactg agat            54

<210> SEQ ID NO 32
<211> LENGTH: 600
<212> TYPE: DNA
<213> ORGANISM: Artificial Sequence
<220> FEATURE:
<223> OTHER INFORMATION: chemically synthesized; D4 plasmid nucleotide

<400> SEQUENCE: 32
aattttgttt aactttaaga aggagatata catatgaaat acctgctgcc gaccgctgct      60
gctggtctgc tgctcctcgc tacccagccg gcgatggccc ttggtaaatt ctcccagacc     120
tgctacaact ccgctatcca gggttccgtt ctgacctcca cctgcgaacg taccaacggt     180
ggttacaaca cctcctccat cgacctgaac tccgttatcg aaaacgttga cggttccctg     240
aaatggcagc cgtccaactt catcgaaacc tgccgtaaca cccagctggc tggttcctcc     300
gaactggctg ctgaatgcaa aacccgtgct cagcagttcg tttccaccaa aatcaacctg     360
```

```
gacgaccaca tcgctaacat cgacggtacc ctgaaatacg aagggtctgg tggcggaggg    420
tcgggcggag gtggaagcgg aggtggcggt agtggtggag gcggatccca tcatcatcat    480
catcatgaca aatgggcaag tttgtggaat tggtttgaaa taacagaatg gctgtggtat    540
ataaaataat aataaaagct tgcggccgca ctcgagcacc accaccacca ccactgagat    600
```

<210> SEQ ID NO 33
<211> LENGTH: 200
<212> TYPE: PRT
<213> ORGANISM: Artificial Sequence
<220> FEATURE:
<223> OTHER INFORMATION: chemically synthesized; D4 plasmid protein
<220> FEATURE:
<221> NAME/KEY: MISC_FEATURE
<222> LOCATION: (4)..(4)
<223> OTHER INFORMATION: ochre stop codon
<220> FEATURE:
<221> NAME/KEY: MISC_FEATURE
<222> LOCATION: (6)..(6)
<223> OTHER INFORMATION: ochre stop codon
<220> FEATURE:
<221> NAME/KEY: MISC_FEATURE
<222> LOCATION: (183)..(183)
<223> OTHER INFORMATION: ochre stop codon
<220> FEATURE:
<221> NAME/KEY: MISC_FEATURE
<222> LOCATION: (184)..(184)
<223> OTHER INFORMATION: ochre stop codon
<220> FEATURE:
<221> NAME/KEY: MISC_FEATURE
<222> LOCATION: (185)..(185)
<223> OTHER INFORMATION: ochre stop codon
<220> FEATURE:
<221> NAME/KEY: MISC_FEATURE
<222> LOCATION: (199)..(199)
<223> OTHER INFORMATION: opal stop codon

<400> SEQUENCE: 33

```
Asn Phe Val Xaa Leu Xaa Glu Gly Asp Ile His Met Lys Tyr Leu Leu
1               5                   10                  15

Pro Thr Ala Ala Ala Gly Leu Leu Leu Ala Thr Gln Pro Ala Met
            20                  25                  30

Ala Leu Gly Lys Phe Ser Gln Thr Cys Tyr Asn Ser Ala Ile Gln Gly
        35                  40                  45

Ser Val Leu Thr Ser Thr Cys Glu Arg Thr Asn Gly Gly Tyr Asn Thr
    50                  55                  60

Ser Ser Ile Asp Leu Asn Ser Val Ile Glu Asn Val Asp Gly Ser Leu
65                  70                  75                  80

Lys Trp Gln Pro Ser Asn Phe Ile Glu Thr Cys Arg Asn Thr Gln Leu
                85                  90                  95

Ala Gly Ser Ser Glu Leu Ala Ala Glu Cys Lys Thr Arg Ala Gln Gln
            100                 105                 110

Phe Val Ser Thr Lys Ile Asn Leu Asp Asp His Ile Ala Asn Ile Asp
        115                 120                 125

Gly Thr Leu Lys Tyr Glu Gly Ser Gly Gly Gly Ser Gly Gly Gly
    130                 135                 140

Gly Ser Gly Gly Gly Gly Ser Gly Gly Gly Ser His His His His
145                 150                 155                 160

His His Asp Lys Trp Ala Ser Leu Trp Asn Trp Phe Glu Ile Thr Glu
                165                 170                 175
```

Trp Leu Trp Tyr Ile Lys Xaa Xaa Xaa Lys Leu Ala Ala Ala Leu Glu
            180                 185                 190

His His His His His His Xaa Asp
        195                 200

<210> SEQ ID NO 34
<211> LENGTH: 6
<212> TYPE: DNA
<213> ORGANISM: Artificial Sequence
<220> FEATURE:
<223> OTHER INFORMATION: chemically synthesized; GS nucleotide

<400> SEQUENCE: 34 ggatcc                                                                 6

<210> SEQ ID NO 35
<211> LENGTH: 634
<212> TYPE: DNA
<213> ORGANISM: Artificial Sequence
<220> FEATURE:
<223> OTHER INFORMATION: chemically synthesized

<400> SEQUENCE: 35
ttaactttaa gaaggagata tacacatgaa atacctgctg ccgaccgctg ctgctggtct      60
gctgctcctc gctacccagc cggcgatgca tatgcctaat ttttcgcaca cttgtagcag     120
tatcaactac gaccctgaca gcacaatcct gagtgctgag tgccaagctc gcgatggaga     180
atggctccct accgaactga ggcttagtga ccatatcggt aatatagatg gggaattgca     240
gttcggggat caaaacttcc aagaaacctg ccaagattgt cgccttgagt tcggggatgg     300
agagcaatcc gtatggttgg tgtgtacttg tcaaacaatg gatggggaat ggaaatctac     360
ccaaatactg ttagacagtc agatcgataa taacgacagc caactggaaa ttggatccgg     420
tggcggaggg tcgggcggag gtgggtccgg tggcggaggt gggtccggtg cggaggtgg      480 gtccggtggc ggagggtcgg gcggaggtgg aagcggaggt ggcggtagtg gtggaggcgg     540 gtccggatcat catcatcatc atgacaaatg ggcaagtttg tggaattggt ttgaaataac     600
agaatggctg tggtatataa aataataata aaag                                 634

<210> SEQ ID NO 36
<211> LENGTH: 199
<212> TYPE: PRT
<213> ORGANISM: Artificial Sequence
<220> FEATURE:
<223> OTHER INFORMATION: chemically synthesized

<400> SEQUENCE: 36

Met Lys Tyr Leu Leu Pro Thr Ala Ala Ala Gly Leu Leu Leu Leu Ala
1               5                   10                  15

Thr Gln Pro Ala Met His Met Pro Asn Phe Ser His Thr Cys Ser Ser
            20                  25                  30

Ile Asn Tyr Asp Pro Asp Ser Thr Ile Leu Ser Ala Glu Cys Gln Ala
        35                  40                  45

Arg Asp Gly Glu Trp Leu Pro Thr Glu Leu Arg Leu Ser Asp His Ile
    50                  55                  60

Gly Asn Ile Asp Gly Glu Leu Gln Phe Gly Asp Gln Asn Phe Gln Glu
65                  70                  75                  80

Thr Cys Gln Asp Cys Arg Leu Glu Phe Gly Asp Gly Glu Gln Ser Val
                85                  90                  95

-continued

```
Trp Leu Val Cys Thr Cys Gln Thr Met Asp Gly Glu Trp Lys Ser Thr
            100                 105                 110

Gln Ile Leu Leu Asp Ser Gln Ile Asp Asn Asn Asp Ser Gln Leu Glu
        115                 120                 125

Ile Gly Ser Gly Gly Gly Gly Ser Gly Gly Gly Gly Ser Gly Gly Gly
    130                 135                 140

Gly Gly Ser Gly Gly Gly Gly Gly Ser Gly Gly Gly Gly Ser Gly Gly
145                 150                 155                 160

Gly Gly Ser Gly Gly Gly Gly Ser Gly Gly Gly Gly Ser His His His
                165                 170                 175

His His His Asp Lys Trp Ala Ser Leu Trp Asn Trp Phe Glu Ile Thr
            180                 185                 190

Glu Trp Leu Trp Tyr Ile Lys
        195
```